United States Patent
Wei

(10) Patent No.: US 9,962,412 B2
(45) Date of Patent: May 8, 2018

(54) COMPOSITIONS AND METHODS OF USE

(71) Applicant: Griffith University, Queensland (AU)

(72) Inventor: Ming Wei, Queensland (AU)

(73) Assignee: Shandong Xinchuang Biotechnology Co., Ltd. (CN)

( * ) Notice: Subject to any disclaimer, the term of this patent is extended or adjusted under 35 U.S.C. 154(b) by 0 days. days.

(21) Appl. No.: 14/397,293

(22) PCT Filed: Apr. 29, 2013

(86) PCT No.: PCT/AU2013/000439
§ 371 (c)(1),
(2) Date: Oct. 27, 2014

(87) PCT Pub. No.: WO2013/159155
PCT Pub. Date: Oct. 31, 2013

(65) Prior Publication Data
US 2015/0147315 A1 May 28, 2015

(30) Foreign Application Priority Data

Apr. 27, 2012 (AU) ................................ 2012901658

(51) Int. Cl.
| | | |
|---|---|---|
| *G01N 33/554* | (2006.01) | |
| *A61K 35/74* | (2015.01) | |
| *C12N 1/20* | (2006.01) | |
| *C12N 1/36* | (2006.01) | |
| *C12R 1/145* | (2006.01) | |
| *A61K 39/395* | (2006.01) | |
| *A61K 39/00* | (2006.01) | |

(52) U.S. Cl.
CPC ........ *A61K 35/74* (2013.01); *A61K 39/39558* (2013.01); *C12N 1/20* (2013.01); *C12N 1/36* (2013.01); *C12R 1/145* (2013.01); *A61K 2039/505* (2013.01)

(58) Field of Classification Search
None
See application file for complete search history.

(56) References Cited

FOREIGN PATENT DOCUMENTS

WO 2002/007741 A1 1/2002

OTHER PUBLICATIONS

V.B.D. Skerman et al., "Approved lists of bacterial names", Int. J. Syst. Bacteriol., vol. 30, pp. 225-420, (1980).
N. Minton, "Clostridia in cancer therapy", Nature Rev. Microbiol., vol. 1, pp. 237-242, (2003).
U. Mohr et al., "Oncolysis by a new strain of clostridium", Cancer Research, vol. 32, pp. 1122-1128, (1972).
S.M. Hashimi et al., "Immunotoxin-mediated targeting of claudin-4 inhibits the proliferation of cancer cells", International Journal of Oncology, vol. 42, pp. 1911-1918, (2013).

*Primary Examiner* — Ja'Na Hines
*Assistant Examiner* — Khatol Shahnan Shah
(74) *Attorney, Agent, or Firm* — Cooley LLP; Ivor R. Elrifi; Matthew Pavao

(57) ABSTRACT

The present invention relates to a derivative bacterial strain of an avirulent, non-pathogenic *Clostridium ghonii* that is capable of arresting the growth of, regressing or destroying one Number of days post cancer cell injection Number of days post cancer cell injection

COMPOSITIONS AND METHODS OF USE

CROSS-REFERENCE TO RELATED APPLICATIONS

This application is a national stage application, filed under 35 U.S.C. § 371, of International Application No. PCT/AU2013/000439, filed on Apr. 29, 2013, which claims the benefit of, and priority to, Australian Patent Application No. 2012901658, filed on Apr. 27, 2012. The contents of each application are incorporated by reference in their entireties.

FIELD OF THE INVENTION

The present invention relates to the creation of a derivative bacterial strain of an avirulent, non-pathogenic *Clostridium ghonii* that is capable of arresting the growth of one or more solid tumours, regressing one or more solid tumours or nearly or completely destroying one or more solid tumours. The present invention further relates to a composition comprising the derivative bacterial strain for targeted lysis of solid tumours.

BACKGROUND ART

The formation of cancer is a multi-stage process that involves a series of molecular and structural alterations. Solid tumours, such as melanoma, lung, colon, head/neck, ovary, breast, pancreatic and prostate cancers, account for 90% of all cancers. The hallmarks of solid tumours at a late stage are extensive angiogenesis, necrosis and hypoxia along with the distinct presence of a central (inner) region and a peripheral region. The central region of a solid tumour characteristically has high interstitial pressure, low extracellular pH, tumour cell heterogeneity and anaerobic metabolisms, including glycolysis with high glucose concentration and lactate state. The peripheral region typically contains rapidly dividing cancer cells although these cells only account for 25-50% of the total cells present in the peripheral region. The remaining cells in the peripheral region are typically non-cancerous stroma cells.

The tumour inner central environments are detrimental for current chemo and radiation therapies as they are denied of passively diffused chemotherapeutic drugs due to poor vascularisation and high interstitial pressure. Furthermore, the deficiency in oxygen radicals also contributes to chemotherapy and radiotherapy resistance and decreasing DNA damage over the course of the treatment.

When a diagnosis is made during the early stage, a curative surgery is the first choice of therapy to remove the cancer followed by radiotherapy and/or chemotherapy to prevent reoccurrence. However, due to lack of specific symptoms in the clinical setting, up to 85% of patients with solid tumours present at an advanced stage where curative surgery is no longer an option. Chemo/radiotherapy or combinations of both were often used as palliative therapy, which fails to improve the overall survival rate of these patients. Chemicals/drugs in the form of antibodies and signal transduction inhibitors have been trialed in preclinical animals for late stage cancer therapy but fail to penetrate solid tumours, unable to accumulate into high concentration, inefficient in reaching a sufficient number of cancer cells, and leaving non-cancer stromal cells, stem cells, and tumour tissue structure untouched. Furthermore, frequent emergence of resistance renders these molecular therapies mostly ineffective.

Gene therapy to treat cancer is considered a better option than the above-mentioned drug therapies. Live virotherapy is considered to be the best approach currently in existence for treating advanced stage solid tumours but have disadvantages such as poor spread through tumors (Shayakhmetov et al., 2002) and rapid hepatic clearance from the circulation after intravenous delivery. Taken together, all of the current available anti-cancer therapies for reducing solid tumours have not met the need for an effective treatment of late stage cancer therapy until now.

Where the tumour central environments, also known as microenvironments, are detrimental for current chemo, radiation, and viro therapies, such environments can provide a unique opportunity for bacterial-based therapy that uses anaerobic bacteria and their innate oncolytic properties. Various anaerobic bacteria have been studied including strains belonging to the genus *Clostridium*. Naturally, *Clostridium* has two growth states; one is vegetative rod, and the other round spore. The latter is a tough, protective form of Clostridial bacterium which helps them survive through difficult times. A spore has a hard coating, wrapping around the outside of the key vital parts of the inside of the bacteria. In addition, there are also membrane layers lining the inside of the wrappings. Together the hard coating and the membrane lining enable the *Clostridium* to survive in tough environments that do not suit the vegetative rod. When growth conditions such as anaerobic environment and more nutrients become abundant, spore will increase gene expression and facilitate regrowth of vegetative rods.

Strict anaerobic proteolytic *Clostridium sporogenes, C. novyi* (include a *novyi*-NT with a major toxicin eliminated, but still has several other toxins and toxic factors) and *C. sordellii* have been shown to specifically target the unique hypoxic/necrotic tumour interior (see FIG. 8), causing modest oncolysis in several cancers when combined with vessel destroying agents. However, these strains are pathogenic microbes, causing various human diseases naturally in which their innate toxicity to humans has caused major issues. These issues are (1) toxicity levels are too high to be acceptable as appropriate therapeutic models for human treatment and (2) the biosafety implication for the use of a pathogenic bacterium for human is difficult to overcome. Furthermore, the wild type strains of *Clostridium novyi* and *C. sordellii* displayed rapid toxicity, resulting in significant death in experimental mice.

The present invention is predicated on the discovery and creation of derived, strictly anaerobic *Clostridium ghonii* strains that have been adapted to possess slower but assured oncolysis and, importantly and surprisingly, are relatively non toxic compared to other clostridial strains. The newly discovered strains are derivatives of an avirulent, non-pathogenic strain of *Clostridium ghonii*. These derived strains of *Clostridium ghonii* are not just useful alternatives to Clostridial strains in the state of the art (e.g. *C. sporogenes, C. novyi* and *C sordeili*), but display fewer toxic side effects than these other Clostridial strains. Without being bound by any biological mechanism or process, the novel adaptation process developed by the inventor and described herein enables the new derived bacterial strains to gain additional ability to leak through defect vessels in the angiogenic/hypoxic/necrotic regions of the solid tumour after intravenous injection of clostridial spores of the present invention, germinate into rod, efficiently and indiscriminately lyse/liquefy various cells as well as the tumour structure (fibronectins and collagens) inside the tumour, thus fundamentally destroying and altering tumour microenvironment. This destruction of the tumour microenvironment effectively arrests tumour growth possibly followed by tumour regression and in some instances eventually leading to the nearly complete or fully complete destruction of the entire tumour. The present invention creates opportunities to combine the approach of using injectable spores with existing approaches to ensure complete elimination of the tumour. As a non-limiting example, one such opportunity is the use of a targeted monoclonal antibody, which otherwise is not effective in the treatment of solid tumour. When a targeted monoclonal antibody is used in a tumour which has part or all of its microenvironment destroyed by the new derived bacterial strains of the present invention, it becomes far more potent because of the newly changed tumour microenvironment. Use of spores of the present invention as described and defined is herein is a clear contribution over the state of the art whether in the form of a single cancer therapy or in combination with another cancer therapy.

SUMMARY OF THE INVENTION

According to a first aspect, the present invention provides a bacterial strain which is derived from an avirulent, non-pathogenic strain of *Clostridium ghonii*, wherein the derived bacterial strain is capable of arresting growth of a solid tumour. The present invention also provides a bacterial strain which is derived from an avirulent, non-pathogenic strain of *Clostridium ghonii*, wherein the derived bacterial strain is capable of regressing or destroying a solid tumour. The strain oncolyses cells contained within the microenvironment of the tumour. The present invention also provides oncolysis of tissue structures contained in the microenvironment by one or more enzymes present in the bacterial cells of the new strains, such as proteinases, lipases and collagenases.

In one embodiment, about 20% to about 90%, or about 20% to about 70%, or about 20% to about 40%, or about 20% to about 35%, or about 25% to about 35% of cells within the microenvironment of the tumour are lysed. In a further embodiment, the derived bacterial strain causes less toxicity than a reference clostridial strain.

In another embodiment, the avirulent, non-pathogenic strain of *Clostridium ghonii* may be selected from the group consisting of ATCC Accession No. 25757, BCRC Accession No. 14548, CCUG Accession No. 9282, DSM Accession No. 15049, NCIMB Accession No. 10636, PEV, Prevot PEV, VPI Accession No. 4897 and VTT Accession No. E-042451.

The bacterial strain of the present invention may be selected from the group consisting of MW-DCG_LCv1, MW-DCG_LCv2, MW-DCG_LCv3, MW-DCG_LCv4, MW-DCG_LCv5, MW-DCG_LCv6, MW-DCG_LCv7, MW-DCG_LCv8, MW-DCG_LCv9, MW-DCG_LCv10, MW-DCG_LCv11, MW-DCG_LCv12, MW-DCG_LCv13, MW-DCG_LCv14, MW-DCG_LCv15, MW-DCG_LCv16, MW-DCG_LCv17, MW-DCG_LCv18, MW-DCG_LCv19, MW-DCG_LCv20, MW-DCG_LCv21, MW-DCG_LCv22, MW-DCG_LCv23, MW-DCG_LCv24, MW-DCG_LCv25, MW-DCG_LCv26, MW-DCG_CCv13, MW-DCG_CCv14, MW-DCG_CCv15, MW-DCG_CCv16, MW-DCG_CCv17, MW-DCG_HNCv13, MW-DCG_HNCv14, MW-DCG_HNCv15, MW-DCG_HNCv16, MW-DCG_HNCv17 and MW-DCG_HNCv18.

The bacteria strains of MW-DCG_LCv1, MW-DCG_LCv2, MW-DCG_LCv3, MW-DCG_LCv4, MW-DCG_LCv5, MW-DCG_LCv6, MW-DCG_LCv7, MW-DCG_LCv8, MW-DCG_LCv9, MW-DCG_LCv10, MW-DCG_LCv11, MW-DCG_LCv12, DCG_HNCv13, MW-DCG_HNCv14, MW-DCG_HNCv15, MW-DCG_HNCv16, MW-DCG_HNCv17 and MW-DCG_HNCv18 have specificity for and are therapeutically effective against solid tumours of head and neck cancer. MW-DCG_HNCv18 is a preferred strain and is represented by the Accession Number V12/001485.

The bacteria strains of MW-DCG_LCv1, MW-DCG_LCv2, MW-DCG_LCv3, MW-DCG_LCv4, MW-DCG_LCv5, MW-DCG_LCv6, MW-DCG_LCv7, MW-DCG_LCv8, MW-DCG_LCv9, MW-DCG_LCv10, MW-DCG_LCv11, MW-DCG_LCv12, MW-DCG_CCv13, MW-DCG_CCv14, MW-DCG_CCv15, MW-DCG_CCv16 and MW-DCG_CCv17 have specificity for and are therapeutically effective against solid tumours of colon cancer. MW-DCG_CCv17 is a preferred strain as represented by Accession Number V12/001487.

The bacteria strains of MW-DCG_LCv1, MW-DCG_LCv2, MW-DCG_LCv3, MW-DCG_LCv4, MW-DCG_LCv5, MW-DCG_LCv6, MW-DCG_LCv7, MW-DCG_LCv8, MW-DCG_LCv9, MW-DCG_LCv10, MW-DCG_LCv11, MW-DCG_LCv12, MW-DCG_LCv13, MW-DCG_LCv14, MW-DCG_LCv15, MW-DCG_LCv16, MW-DCG_LCv17, MW-DCG_LCv18, MW-DCG_LCv19, MW-DCG_LCv20, MW-DCG_LCv21, MW-DCG_LCv22, MW-DCG_LCv23, MW-DCG_LCv24, MW-DCG_LCv25 and MW-DCG_LCv26 have specificity for and are therapeutically effective against solid tumours of lung cancer. MW-DCG_LCv26 is a preferred strain as represented by Accession Number V12/001486.

According to a second aspect, the present invention provides clostridial spores of one or more bacterial strains of the first aspect. In one embodiment, the clostridial spores of the second aspect may be combined with a physiologically acceptable carrier and/or excipient.

According to a third aspect, the present invention provides a method of arresting the growth of, regressing or destroying one or more solid malignant tumours in a subject, wherein the method comprises administration of a therapeutically effective amount of the clostridial spores of the second aspect to the subject in need thereof.

According to a fourth aspect, the present invention provides use of the clostridial spores of the second aspect to arrest the growth of, regress or destroy one or more solid tumours in a subject, wherein a therapeutically effective amount of the clostridial spores of the second aspect is administered to the subject in need thereof.

According to a fifth aspect, the present invention provides a method of treating one or more solid malignant tumours in a subject, wherein growth arrest of the one or more tumours, tumour regression or tumour destruction is indicative of the treatment, wherein the method comprises administration of
(1) a therapeutically effective amount of the clostridial spores of the second aspect and
(2) a therapeutically effective amount of an anti-cancer agent to the subject.

According to a sixth aspect, the present invention provides use of the clostridial spores of the second aspect and an anti-cancer agent in a combination therapy for treating one or more solid malignant tumours in a subject, wherein growth arrest of one or more of the tumours, tumour regression or tumour destruction is indicative of the treatment, wherein (1) a therapeutically effective amount of the clostridial spores of the second aspect and (2) a therapeutically effective amount of the anti-cancer agent is administered to the subject in need thereof.

In an embodiment of the fifth and sixth aspects, the administration of (1) and (2) to the subject occurs either sequentially or simultaneously. (1) and (2) may be administered as one pharmaceutical composition to the subject. Administration of (1) and (2), either as one composition or separately, may be repeated one or more times to ensure tumour regression. For example, (1) and (2) may be administered to the subject as a first dose followed by administration of (2) alone as a second dose. More than one anti-cancer agent may be administered in any number of doses.

In another embodiment, (1) is clostridial spores of MW-DCG_HNCv18 and (2) is a chimeric anti-EGFR monoclonal antibody. In a further embodiment, (2) is Cetuximab. In yet another embodiment, the clostridial spores of MW-DCG_HNCv18 and Cetuximab are administered simultaneously to the subject followed by a second administration of Cetuximab alone.

In one embodiment of the third, fourth, fifth and sixth aspects, the therapeutically effective amount of the clostridial spores of the second aspect is about $10^6$ colony-forming units (CFU) to about $10^{14}$ CFU/kg per dose. In a further embodiment, the therapeutically effective amount of the clostridial spores of the second aspect is about $10^8$-$10^{12}$ or about $10^9$-$10^{11}$ CFU/kg per dose. In another embodiment, the therapeutically effective amount of the clostridial spores of the second aspect is about $10^{10}$-$10^{11}$ CFU/kg per dose. In yet another embodiment, the therapeutically effective amount of the clostridial spores of the second aspect is about $10^{10.5}$ CFU/kg per dose. Administration of the therapeutically effective amount of the clostridial spores of the second aspect to the subject may be via intravenous, intraspinal, subcutaneous or intramuscular. For example, administration may be intravenous.

According to a seventh aspect, the present invention provides a pharmaceutical composition comprising the clostridial spores of the second aspect and a physiologically acceptable carrier and/or excipient. The composition may further comprise an anti-cancer agent. The anti-cancer agent may be an agent as defined under the fifth and sixth aspects.

The anti-cancer agent is any agent that may be used in chemotherapy, radiation, or antibody-based therapies or combinations thereof. The agent may be one or more chemicals, one or more RNA molecules, one or more antibodies or any combination thereof.

For example, the one or more chemicals may be sodium dichloroacetate, paclitaxel, doxil, topotecan, DNA-altering drugs, carboplatin, antimetabolites, gemcitabine, drugs that prevent cell division, vincristine, anti-angiogenic agents, and pazopanib.

An example of the one or more RNA molecules is a small interference RNA (siRNA). The siRNA may be specific for lactate dehydrogenase A (LDHA) or specific for CD147.

An example of the one or more antibodies is an anti-cancer monoclonal antibody. An anti-cancer antibody may be an anti-immune stimulation antibody or an anti-T reg monoclonal antibody. An example of an anti-immune stimulation antibody is an anti-CD40 monoclonal antibody. The anti-CD40 monoclonal antibody may be FGK45. An example of an anti-T reg monoclonal antibody is an anti-CD25 monoclonal antibody. The anti-CD25 monoclonal antibody may be PC61. In another embodiment, the agent is targeting anti-epidermal growth factor receptor (EGFR).

The anti-cancer monoclonal antibody may be conjugated or naked. Naked antibodies, for example, have an effect such as by complement-mediated cytolysis and antibody-dependent, cell-mediated cytotoxicity. Conjugated antibodies include antibodies that are conjugated to a radioisotope or a drug-activating enzyme. The radioactively conjugated antibody may be used in radioimmunotherapy. Examples of a radioactively conjugated antibody or radioisotope is rhenium-188 or rhenium-186, fluorodeoxyglucose ($^{18}$F) also known as FDG, yttrium 90 ($^{90}$Y)-conjugated anti-CD20 antibody $Y^{90}$-ibritumomab tiuxetan and the iodine 131 ($^{131}$I)-conjugated anti-CD20 antibody $I^{131}$-tositumomab. Antibodies conjugated to a drug-activating enzyme may be used in antibody-directed enzyme prodrug therapy (AD-EPT). The anti-cancer monoclonal antibody may be conjugated to a liposome or nanoparticle and include within the liposome or nanoparticle various drugs and therapeutic nucleotides, such as siRNAs.

The method accordingly to the fifth aspect and the use accordingly to the sixth aspect may further include hormone therapy, hyperthermia, surgery, radiation or any combination thereof as an alternative or in addition to the administration of one or more anti-cancer agents. Radiation may be ionizing radiation.

According to an eighth aspect, the present invention provides a process of deriving a bacterial strain from an avirulent, non-pathogenic strain of *Clostridium ghonii*, wherein the derived bacterial strain produced by the process is capable of arresting the growth of, regressing or destroying one or more solid tumour by oncolysis of cells within the microenvironment of the one or more tumours, wherein the derived bacterial strain produced by the process causes less toxicity than a reference clostridial strain.

In one embodiment, the process of deriving a bacterial strain from an avirulent, non-pathogenic strain of *Clostridium ghonii*, comprises:

(1) Preparing injectable clostridial spores from the avirulent, non-pathogenic strain of *Clostridium ghonii* comprising
  (a) inoculating vegetative rods of the bacterial strain of (1) into sporulation medium,
  (b) allowing sufficient time and conditions for sporulation of the rods, and
  (c) purifying the spores;
(2) Injecting the purified clostridial spores of (1) into an animal that supports growth of a solid tumour;
(3) Assessing parameters to determine rate and degree of oncolysis and toxicity;
(4) Collecting vegetative rods from the tumour of (2) by harvesting the tumour;
(5) Streaking out the rods of (4) onto an agar plate;
(6) Selecting two or more single colonies from the plate of (5) and inoculating a broth culture to grow vegetative rods; and
(7) Repeating steps (1)(a) to (6) between about 10 to about 35 times.

In another embodiment, the two or more single colonies of (6) are three single colonies.

In another embodiment, steps (1)(a) to (6) are repeated about 15 to about 30 times, or about 17 to about 26 times.

In another embodiment, the parameters of (3) may comprise time of spore colonisation, oncolysis, pus formation and burst, tumour volume, systemic toxicity, animal survival, number of spores/rods isolated from the tumours after intravenous administration of spores or any combination thereof.

In another embodiment, the bacterial strain lyses about 20% to about 90%, or about 20% to about 70%, or about 20% to about 40%, or about 20% to about 35%, or about 25% to about 35% of cells within the microenvironment of the tumour. In another embodiment, the avirulent, non-pathogenic strain of *Clostridium ghonii* may be selected from the group consisting of ATCC Accession No. 25757, BCRC Accession No. 14548, CCUG Accession No. 9282, DSM Accession No. 15049, NCIMB Accession No. 10636, PEV, Prevot PEV, VPI Accession No. 4897 and VTT Accession No. E-042451.

According to a ninth aspect, the present invention provides a kit for the treatment of one or more solid malignant tumours comprising the bacterial strain of the first aspect, clostridial spores of the second aspect or the pharmaceutical composition of the seventh aspect, further comprising an anti-cancer agent and instructions for use.

In an embodiment of any one or more of the preceding aspects, the subject may be a mammal. The mammal may be a human.

In an embodiment of any one or more of the preceding aspects, the solid malignant tumor is selected from the group consisting of respiratory system carcinomas, gastrointestinal system carcinomas, genitourinary system carcinomas, testicular carcinomas, breast carcinomas, prostate carcinomas, endocrine system carcinomas, melanomas, choriocarcinoma, and carcinomas of the cervix, lung, head and neck, colon, ovary, brain, bladder, breast, prostate, tumors of bone, fat, and cartilage, Hodgkin's disease, non-Hodgkin's lymphoma, B cell lymphoma, epitheliotropic lymphoma, composite lymphoma, anaplastic large cell lymphoma, gastric and non-gastric mucosa-associated lymphoid tissue lymphoma, lymphoproliferative disease, T cell lymphoma, Burkitt's lymphoma, mantle cell lymphoma, diffuse large cell lymphoma, lymphoplasmacytoid lymphoma, and multiple myeloma.

Definitions

In the context of this specification, the term "comprising" means "including principally, but not necessarily solely". Furthermore, variations of the word "comprising", such as "comprise" and "comprises", have correspondingly varied meanings.

The term "strain" means a subset of a bacterial species differing from other bacteria of the same species by one or more minor but identifiable differences. A strain is "a population of organisms that descends from a single organism or pure culture isolate. Strains within a species may differ slightly from one another in many ways." (p. 392, Prescott et al., 1996). Strains are often created in the laboratory by mutagenising existing strains or wild-type examples of bacterial species.

As used herein, the term "derivative" is any bacterial strain derived from an avirulent, non-pathogenic *Clostidium ghonii* such as, but not limited to, ATCC Accession No. 25757, BCRC Accession No. 14548, CCUG Accession No. 9282, DSM Accession No. 15049, NCIMB Accession No. 10636, PEV, Prevot PEV, VPI Accession No. 4897 and VTT Accession No. E-042451, whereby derivation was achieved through serial selection, isolation and inoculation steps with a xenograft solid tumour in an animal, whereby oncolysis of the tumour is observed and toxicity to the animal is insignificant.

As used herein, the terms "necrotic area", "hypoxic area", "central environment" and "microenvironment" are interchangeable and refer to the inside of a solid tumour that has one or more of the following characteristics: having high interstitial pressure, low extracellular pH, tumour cell heterogeneity and anaerobic metabolisms, including glycolysis with high glucose concentration and lactate state.

As used herein, the term "isolated" or "isolation" means that the bacterial cells have been removed or collected from culture plates or from its natural environment or host (e.g. tumour).

As used herein, the phrase "less toxicity than a reference clostridial strain" and "causes less toxicity than a reference clostridial strain" means the growth of a derived clostridial strain inside a solid tumour of a subject and subsequent oncolysis produces less toxicity to the subject compared to a subject that has been inoculated with a reference clostridial strain whereby the reference strain may be, but not limited to, a saccharolytic species, the proteolytic *C. sporogenes*, proteolytic *C. novyi*-NT and *C. sordellii* or even *C. ghonii* that has either not been derived by the process of the present invention or as only been through the adapation process once. Toxicity level is defined and scored using a comprehensive score sheet including the following four levels: Appearance; Clinical Signs; Unprovoked behaviour; and Behavioral responses to external stimuli.

The term "cancer" includes malignancies characterized by deregulated or uncontrolled cell growth such as solid malignancies that may form as a carcinoma, a sarcoma, or lymphoma. The term "cancer" includes primary malignant tumors, e.g., those whose cells have not migrated to sites in the subject's body other than the site of the original tumor, and secondary malignant tumors, e.g., those arising from metastasis, the migration of tumor cells to secondary sites that are different from the site of the original tumor.

As used herein, the term "solid tumour" is an abnormal mass of tissue that usually does not contain cysts or liquid areas. Solid tumours may be benign or malignant. Solid tumours as contemplated herein are malignant tumours. Sarcomas, carcinomas, and lymphomas may be associated with solid tumours. Leukemias generally do not form solid tumours.

As used herein, the term "carcinoma" means any malignancy of epithelial or endocrine tissues, including respiratory system carcinomas, gastrointestinal system carcinomas, genitourinary system carcinomas, testicular carcinomas, breast carcinomas, prostate carcinomas, endocrine system carcinomas, melanomas, choriocarcinoma, and carcinomas of the cervix, lung, head and neck, colon, and ovary.

As used herein, the term "sarcoma" means any malignant tumors of mesodermal connective tissue, for example, tumors of bone, fat, and cartilage.

As used herein, the term "lymphoma" means any malignancy of hematopoietic cells of the bone marrow. These malignancies usually manifest as solid tumours. Examples of lymphomas include Hodgkin's disease, non-Hodgkin's lymphoma, B cell lymphoma, epitheliotropic lymphoma, composite lymphoma, anaplastic large cell lymphoma, gastric and non-gastric mucosa-associated lymphoid tissue lymphoma, lymphoproliferative disease, T cell lymphoma, Burkitt's lymphoma, mantle cell lymphoma, diffuse large cell lymphoma, lymphoplasmacytoid lymphoma, and multiple myeloma.

As used herein, the term "arrest" means the tumour has stopped growing.

As used herein, the term "tumour regression" means the shrinking of solid tumours following administration of clostridial spores of the present invention alone or in combination with an anti-cancer agent and/or an additional anti-cancer therapy. To determine tumour regression, the size of a treated and untreated (control) tumour are taken at a specific time point and compared to each other. Both "arrest" and "regression" may or may not eventually lead to tumour destruction.

As used herein, the term "subject" means organisms which are capable of suffering from cancer, particularly in the form of solid tumors. The organisms may by mammals and include human and various non-human animals, such as primates, dogs and cats. Preferred human animals include human subjects. As contemplated herein, the subject may be at greater risk of having solid malignant tumours develop within their bodies compared to the average member of a population.

As used herein the terms "treatment", "treating" and variations thereof, refer to any and all uses which remedy a disease state or symptoms, prevent the establishment of disease, or otherwise prevent, hinder, retard, or reverse the progression of disease or other undesirable symptoms in any way whatsoever. As contemplated herein, treatment of a solid tumour means growth arrest, regression or nearly complete or complete destruction of the tumour.

As used herein the term "effective amount" includes within its meaning a non-toxic but sufficient amount of an entity per se to provide the desired therapeutic or prophylactic effect. The exact amount required will vary from subject to subject depending on factors such as the species being treated, the age and general condition of the subject, the severity of the condition being treated, the particular entity being administered and the mode of administration and so forth. Thus, it is not possible to specify an exact "effective amount". However, for any given case, an appropriate "effective amount" may be determined by one of ordinary skill in the art using only routine experimentation. Specifically, the terms "effective amount" and "therapeutically effective amount" refer synonymously to that amount of a composition or dosage unit which in a patient population has the effect of (1) reducing the size of the tumor; (2) inhibiting (that is, slowing to some extent, preferably stopping) tumor metastasis; (3) inhibiting to some extent (that is slowing to some extent, preferably arresting) tumor growth; and/or; (4) relieving to some extent (or preferably eliminating) one or more symptoms associated with cancer; (5) nearly complete or complete destruction of a tumor; (6) extending the time of disease progression; and/or (7) improving overall survival.

As used herein, a "pharmaceutical composition" refers to clostridial spores alone or in one or more of the combinations described herein. In one embodiment, the combination is clostridial spores of the derived bacterial strains of the present invention and one or more anti-cancer agents that may be known in the art. Other chemical components, such as physiologically acceptable carriers and excipients, are also contemplated herein.

As used herein, the term "pharmaceutically acceptable" means that the agent or excipient is generally regarded as acceptable for use in a pharmaceutical composition.

As used herein, a "physiologically acceptable carrier" refers to a carrier or diluent that does not cause significant irritation to an organism and does not abrogate the biological activity and properties of the administered composition. Exemplary pharmaceutically acceptable carriers include solid and liquid diluents. Water, ethanol, propylene glycol, and glycerol are illustrative pharmaceutically acceptable liquid diluents; of these, water is preferred in some embodiments.

As used herein, an "excipient" refers to a pharmaceutically inert substance added to a pharmaceutical composition to further facilitate administration of a pharmaceutical composition of this invention. Examples, without limitation, of excipients include calcium carbonate, calcium phosphate, various sugars and types of starch, cellulose derivatives, gelatin, vegetable oils and polyethylene glycols. The groups of excipients and active pharmaceutical ingredients are considered mutually exclusive in the pharmaceutical arts.

Figure 7:
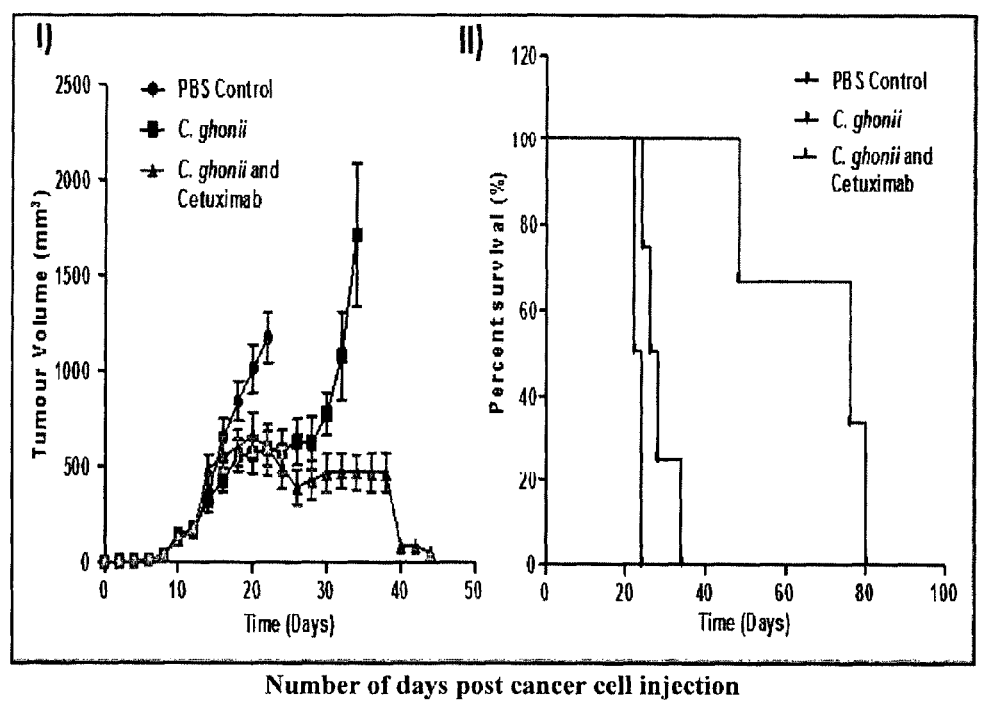

FIG. 7. (I). Anticancer therapeutic effects. Mice were randomly grouped. On day 16, group 1 was administered with PBS, Group 2 and 3 with DCG spores. Group 3 was further administered with Cetuximab. Tumour volume was recorded every other day. (II). Percentage of animal survival. Three groups were presented.

Figure 8:
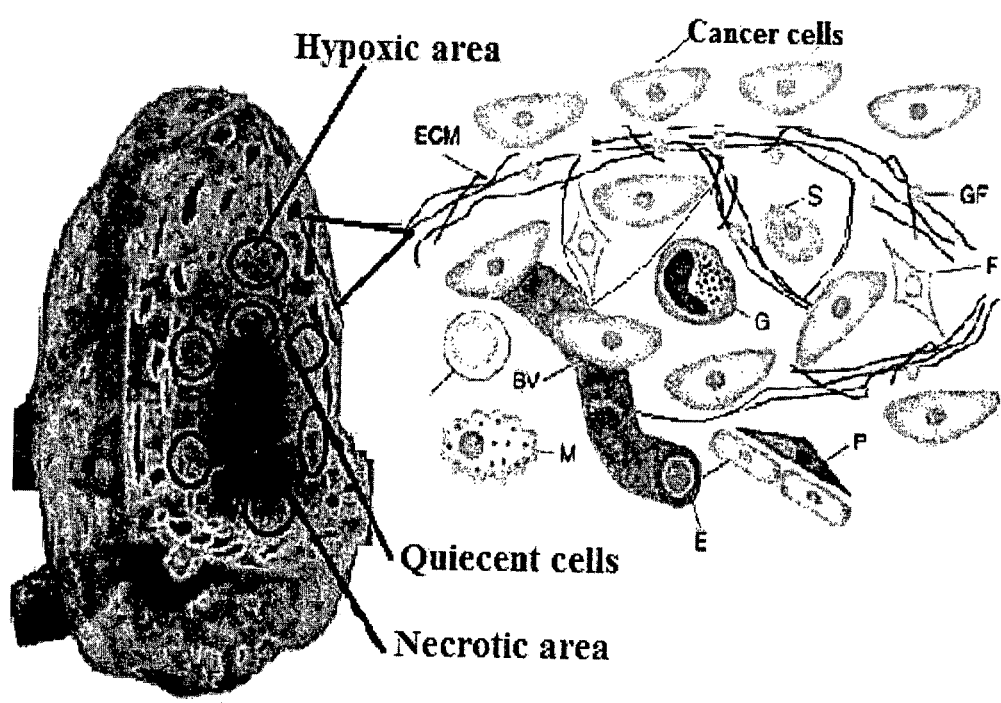

FIG. 8: Schematic diagram showing liquefying tumour from within and killing viable cancer cells from outside (in the rim). This approach is a conceptual change in the development of cancer therapy.

Figure 9:
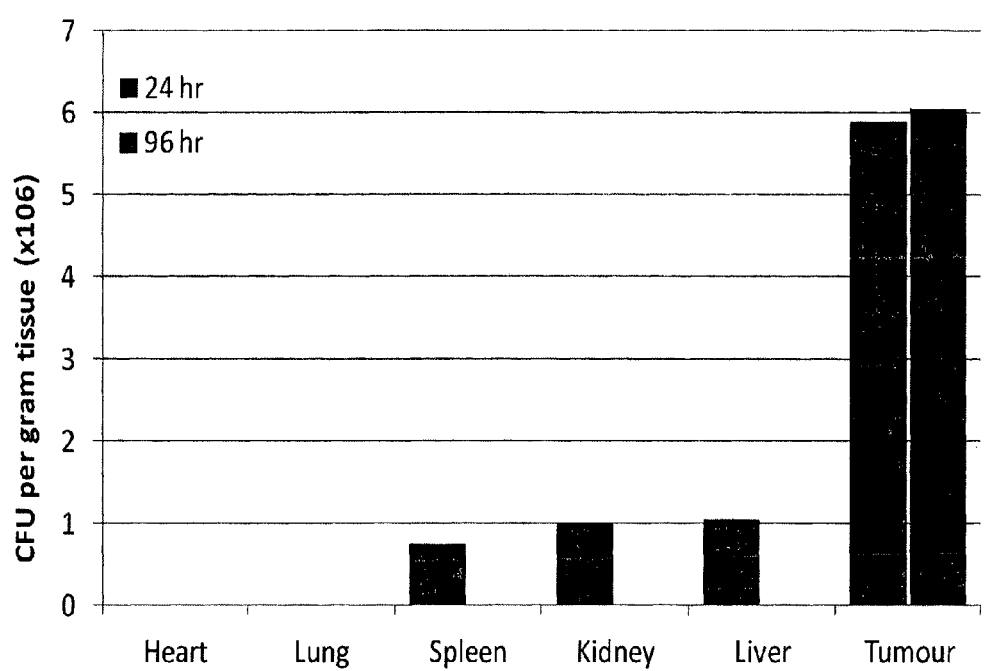

FIG. 9. Specificity of tumour colonisation of strain MW-DCG_LCv26. The spores of MW-DCG_LCv26 were injected intravenously into mice bearing subcutaneous NSCLC at a dose of $10^8$ CFU/kg per mouse. Tissue from the tumour and non-cancerous tissue from the heart, lung, spleen, kidney and liver were collected after the spores were allowed to germinate for 24 and 96 hours post injection. Half of the collected tissue was homogenized and tested for the presence of spores by enumerating germination of the spores.

Figure 10:

FIG. 10. Photographic representations of NSCLC after spore delivery showing specific colonisation and tumour oncolysis. Panel a shows a NSCLC from a mouse that has not been injected—i.e. no injection control. Panel b shows a NSCLC from a mouse that has been injected with PBS-PBS control. Panel c shows a NSCLC from a mouse that has been intravenously injected with spores of the strain MW-DCGLCv26.

Figure 11:
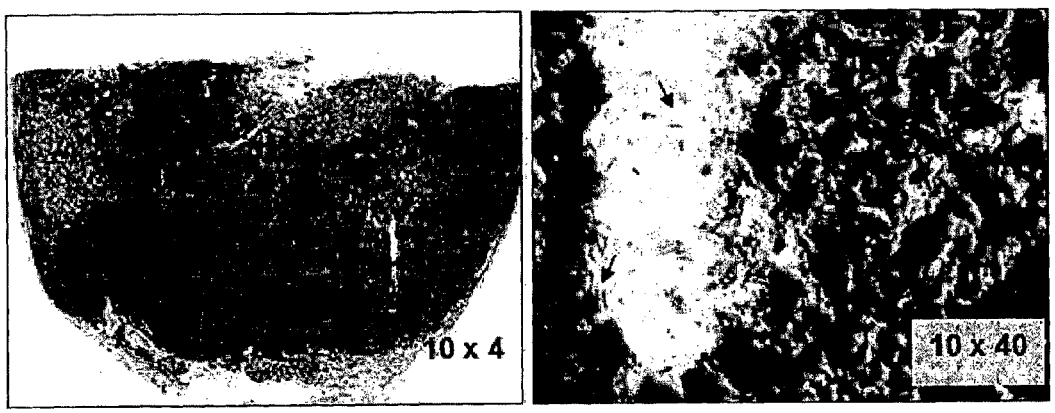

FIG. 11. Photographic representations of gram positive stained MW-DCG_LCv26 rods within necrotic/hypoxic regions of a NSCLC removed from a mouse that has been intravenously injected with spores of MW-DCG_LCv26. Slices of the NSCLC were made and fixed to cover slides. Gram staining was performed. Stained slices were observed and pictorial captured at a magnification of 10×4. Arrows indicate the presence of rods of MW-DCG_LCv26.

DETAILED DESCRIPTION

The description below fully supports and describes the present invention which relates to the identification of new strains derived from *Clostridium ghonii* that are efficient, but moderate oncolysers. These strains are so unique that they solve the problem of fast oncolysis of other strains that results in significant toxicity and non usage in a clinical setting. The new derived strains of *Clostridium ghonii* were discovered by a new method of repeatedly adapting an avirulent *C. ghonii* strain in solid experimental cancers of xenograft (human cancers) and synergeic mouse cancers, such as but not limited to lung, colon, head and neck, breast, and melanoma which demonstrates oncolytic therapeutical efficacy of the adapted *C. ghonii* in the above-mentioned cancers.

The greatest effectiveness of the new strains lies in oncolysis of the microenvironment (central area) of solid malignant tumours whilst resulting in little to no toxicity. Within their scope, the new strains have the oncolytic ability to lyse viable cancerous cells as well as lyse tissue structures contained in the microenvironment. Lysis of the tissue structures of the microenvironment is provided by enzymes within the bacterial cells of the new strains. For example, bacterial proteinases, lipases and collagenases of the new strains are effective in lysing the tissue structures which comprise inter alia fibronectin and collagen. This is a clear advantage over viral oncolysis as viruses do not possess such enzymes to lyse the tissue structures and thus are only limited to oncolysis of viable cells.

As contemplated herein, the solid tumours may be in form a carcinoma, a sarcoma, or lymphoma. These solid tumours may be primary, as in, a mass of cells that have not migrated to sites in the subject's body other than the site of the original tumor, or secondary, i.e. mass of cells that arise from metastasis in which the migration of tumor cells to secondary sites are different from the site of the original tumor. Any solid tumour which is affected by the clostridial spores of the new derived bacterial strains of the present invention in terms of oncolysis, destruction of the microenvironment, growth arrest, tumour regression, and nearly complete or complete tumour destruction is contemplated herein. Solid tumours as defined herein are considered to be an abnormal mass of tissue that usually does not contain cysts or liquid areas. As contemplated herein, the solid tumour may be in the form of respiratory system carcinomas, gastrointestinal system carcinomas, genitourinary system carcinomas, testicular carcinomas, breast carcinomas, prostate carcinomas, endocrine system carcinomas, melanomas, choriocarcinoma, carcinomas of the cervix, lung, head and neck, colon, and ovary, tumors of bone, fat, and cartilage, Hodgkin's disease, non-Hodgkin's lymphoma, B cell lymphoma, epitheliotropic lymphoma, composite lymphoma, anaplastic large cell lymphoma, gastric and non-gastric mucosa-associated lymphoid tissue lymphoma, lymphoproliferative disease, T cell lymphoma, Burkitt's lymphoma, mantle cell lymphoma, diffuse large cell lymphoma, lymphoplasmacytoid lymphoma, and multiple myeloma.

The therapeutic methods and uses of the present invention can be applied to cancerous cells of mesenchymal origin, such as those producing sarcomas (e.g., fibrosarcoma, myxosarcoma, liosarcoma, chondrosarcoma, osteogenic sarcoma or chordosarcoma, angiosarcoma, endotheliosardcoma, lympangiosarcoma, synoviosarcoma or mesothelisosarcoma); leukemias and lymphomas such as granulocytic leukemia, monocytic leukemia, lymphocytic leukemia, malignant lymphoma, plasmocytoma, reticulum cell sarcoma, or Hodgkin's disease; sarcomas such as leiomysarcoma or rhabdomysarcoma, tumors of epithelial origin such as squamous cell carcinoma, basal cell carcinoma, sweat gland carcinoma, sebaceous gland carcinoma, adenocarcinoma, papillary carcinoma, papillary adenocarcinoma, cystadenocarcinoma, medullary carcinoma, undifferentiated carcinoma, bronchogenic carcinoma, melanoma, renal cell carcinoma, hepatoma-liver cell carcinoma, bile duct carcinoma, cholangiocarcinoma, papillary carcinoma, transitional cell carcinoma, chorioaencinoma, semonoma, or embryonal carcinoma; and tumors of the nervous system including gioma, menigoma, medulloblastoma, schwannoma or epidymoma. Additional cell types amenable to treatment according to the methods described herein include those giving rise to mammary carcinomas, gastrointestinal carcinoma, such as colonic carcinomas, bladder carcinoma, prostate carcinoma, and squamous cell carcinoma of the neck and head region. Examples of cancers amenable to treatment according to the methods described herein include vaginal, cervical, liver, kidney and breast cancers, and melanomas.

The effectiveness of the new derived bacterial strains is shown and supported in experimental data as presented in the Examples. For example, injecting clostridia (spores from the new derived bacterial strains of the present invention into mice resulted in near-complete lysis in 30% of the mice bearing advanced lung, colon, Head and Neck and melanoma cancers. The lysis includes destruction of tumour structure, and cellular mass, turning solid masses into liquid, which upon infiltration of white blood cells, become pus like liquid. These tumours typically disappeared. The remaining mice exhibit extensive central oncolysis in their tumours, the skin colour turns to red, and then black, with some of these that eventually burst through skins. But these were incomplete due to the tumour's oxygen-rich edge, leaving a thin layer of peripheral rim which contains viable, typical rapid dividing cancer cells. From this, the inventors have discovered that a combinatorial therapy approach would augment oncolysis and contemplate use of additional therapies to enhance oncolytic efficacy. As contemplated herein, the combination therapy comprises administration of clostridial spores of the present invention and an anti-cancer agent to a subject in need of treatment of a solid tumour. Alternatively or in addition to administration of the anti-cancer agent is hormone therapy, hyperthermia, surgery, radiation or any combination thereof. The combination approach as described and defined herein leads to growth arrest of solid malignant tumours such as tumours of lung, colon, and Head and Neck cancer, tumour regression of the tumours and eventually tumour destruction.

Derived Bacterial Strains

As contemplated herein, the present invention provides a bacterial strain which is derived from an avirulent, non-pathogenic strain of *Clostridium ghonii*, wherein the bacterial strain is capable of arresting growth of a solid tumour by oncolysis of cells contained within the microenvironment of the tumour. About 20% to about 90%, or about 20% to about 70%, or about 20% to about 40%, or about 20% to about 35%, or about 25% to about 35% of cells within the microenvironment of the tumour are lysed by the bacterial strains of the present invention which cause less toxicity than a reference clostridial strain. The avirulent, non-pathogenic strain of *Clostridium ghonii* could be any strain that allows for the working of the invention and is contemplated within the spirit of the invention. For example, the avirulent strain used could be ATCC Accession No. 25757, BCRC Accession No. 14548, CCUG Accession No. 9282, DSM Accession No. 15049, NCIMB Accession No. 10636, PEV, Prevot PEV, VPI Accession No. 4897 or VTT Accession No. E-042451.

Non-limiting examples of the bacterial strains of the present invention are MW-DCG_LCv1, MW-DCG_LCv2, MW-DCG_LCv3, MW-DCG_LCv4, MW-DCG_LCv5, MW-DCG_LCv6, MW-DCG_LCv7, MW-DCG_LCv8, MW-DCG_LCv9, MW-DCG_LCv10, MW-DCG_LCv11, MW-DCG_LCv12, MW-DCG_LCv13, MW-DCG_LCv14, MW-DCG_LCv15, MW-DCG_LCv16, MW-DCG_LCv17, MW-DCG_LCv18, MW-DCG_LCv19, MW-DCG_LCv20, MW-DCG_LCv21, MW-DCG_LCv22, MW-DCG_LCv23, MW-DCG_LCv24, MW-DCG_LCv25, MW-DCG_LCv26, MW-DCG_CCv13, MW-DCG_CCv14, MW-DCG_CCv15, MW-DCG_CCv16, MW-DCG_CCv17, MW-DCG_HNCv13, MW-DCG_HNCv14, MW-DCG_HNCv15, MW-DCG_HNCv16, MW-DCG_HNCv17 and MW-DCG_HNCv18. The bacteria strains of MW-DCG_LCv1, MW-DCG_LCv2, MW-DCG_LCv3, MW-DCG_LCv4, MW-DCG_LCv5, MW-DCG_LCv6, MW-DCG_LCv7, MW-DCG_LCv8, MW-DCG_LCv9, MW-DCG_LCv10, MW-DCG_LCv11, MW-DCG_LCv12, DCG_HNCv13, MW-DCG_HNCv14, MW-DCG_HNCv15, MW-DCG_HNCv16, MW-DCG_HNCv17 and MW-DCG_HNCv18 have specificity for and are therapeutically effective against solid tumours of head and neck cancer. MW-DCG_HNCv18 is a preferred strain. MW-DCG_HNCv18 was deposited with the National Measurement Institute, 1/153 Bertie Street, Port Melbourne, Victoria, Australia 3207 in the capacity of an International Depository Authority on 18 Apr. 2012 and was given the Accession Number V12/001485.

The bacteria strains of MW-DCG_LCv1, MW-DCG_LCv2, MW-DCG_LCv3, MW-DCG_LCv4, MW-DCG_LCv5, MW-DCG_LCv6, MW-DCG_LCv7, MW-DCG_LCv8, MW-DCG_LCv9, MW-DCG_LCv10, MW-DCG_LCv11, MW-DCG_LCv12, MW-DCG_CCv13, MW-DCG_CCv14, MW-DCG_CCv15, MW-DCG_CCv16 and MW-DCG_CCv17 have specificity for and are therapeutically effective against solid tumours of colon cancer. MW-DCG_CCv17 is a preferred strain. MW-DCG_CCv17 was deposited with the National Measurement Institute, 1/153 Bertie Street, Port Melbourne, Victoria, Australia 3207 in the capacity of an International Depository Authority on 18 Apr. 2012 and was given the Accession Number V12/001487.

The bacteria strains of MW-DCG_LCv1, MW-DCG_LCv2, MW-DCG_LCv3, MW-DCG_LCv4, MW-DCG_LCv5, MW-DCG_LCv6, MW-DCG_LCv7, MW-DCG_LCv8, MW-DCG_LCv9, MW-DCG_LCv10, MW-DCG_LCv11, MW-DCG_LCv12, MW-DCG_LCv13, MW-DCG_LCv14, MW-DCG_LCv15, MW-DCG_LCv16, MW-DCG_LCv17, MW-DCG_LCv18, MW-DCG_LCv19, MW-DCG_LCv20, MW-DCG_LCv21, MW-DCG_LCv22, MW-DCG_LCv23, MW-DCG_LCv24, MW-DCG_LCv25 and MW-DCG_LCv26 have specificity for and are therapeutically effective against solid tumours of lung cancer. MW-DCG_LCv26 is a preferred strain. MW-DCG_LCv26 was deposited with the National Measurement Institute, 1/153 Bertie Street, Port Melbourne, Victoria, Australia 3207 in the capacity of an International Depository Authority on 18 Apr. 2012 and was given the Accession Number V12/001486.

Clostridial Spores

As contemplated herein, the present invention provides clostridial spores of one or more bacterial strains described throughout the specification. These clostridial spores may be combined with a physiologically acceptable carrier and/or excipient. Any known carrier or excipient is contemplated herein.

Arresting Growth of the Tumour, Tumour Regression and Tumour Destruction

As contemplated herein, the present invention provides a method of arresting growth of, regressing or destroying one or more solid malignant tumours in a subject, wherein the method comprises administration of a therapeutically effective amount of clostridial spores as described herein to the subject in need thereof. There is also contemplation of use of the clostridial spores in the same or similar manner.

Combinatorial Therapy

There is contemplation of a combinatorial therapy for treating one or more solid malignant tumours in a subject, wherein growth arrest, tumour regression or tumour destruction is indicative of the treatment, wherein the method comprises administration of (1) a therapeutically effective amount of the clostridial spores of the second aspect and (2) a therapeutically effective amount of an anti-cancer agent to the subject. There is also contemplation of use of the clostridial spores and an anti-cancer agent in the same or similar manner. The administration of (1) and (2) to the subject occurs either sequentially or simultaneously. (1) and (2) may be administered as one pharmaceutical composition to the subject, Administration of (1) and (2), either as one composition or separately, may be repeated one or more times to ensure tumour regression. For example, (1) and (2) may be administered to the subject as a first dose followed by administration of (2) alone as a second dose. More than one anti-cancer agent may be administered in any number of doses. For example, (1) is clostridial spores of MW-DCG_HNCv18 and (2) is an anti EGFR agent. In one example, (2) is an anti-EGFR monoclonal antibody or EGFR tyrosine kinase inhibitor. In a further example, (2) is Cetuximab. In yet a further example, as per Example 3, it is contemplated that the clostridial spores of MW-DCG_HNCv18 and Cetuximab are administered simultaneously to the subject followed by a second administration of Cetuximab alone however any combination of spores of the present invention and the anti-cancer agent(s) in any number of doses and formulations is within the scope and spirit of the invention. Also within the spirit and scope of the invention is the use of other anti-cancer treatments known in the art as part of the combinatorial therapy described herein, such treatments include, but are not limited to hormone therapy, hyperthermia, surgery and radiation.

Process of Deriving Bacterial Strains (Adaption)

As contemplated herein, the present invention provides a process of deriving a bacterial strain from an avirulent, non-pathogenic strain of *Clostridium ghonii*, wherein the derived bacterial strain produced by the process is capable of arresting growth of, regressing or destroying a solid tumour by oncolysis of cells within the microenvironment of the tumour, wherein the derived bacterial strain produced by the process causes less toxicity than a reference clostridial strain. The process includes:

(1) Preparing injectable clostridial spores from the avirulent, non-pathogenic strain of *Clostridium ghonii* comprising (a) inoculating, vegetative rods of the bacterial strain of (1) into sporulation medium, (b) allowing sufficient time and conditions for sporulation of the rods, and (c) purifying the spores;

(2) Injecting the purified clostridial spores of (1) into an animal that supports growth of a solid tumour;

(3) Assessing parameters to determine rate and degree of oncolysis and toxicity;

(4) Collecting vegetative rods from the tumour of (2) by harvesting the tumour;

(5) Streaking out the rods of (4) onto an agar plate;

(6) Selecting two or more single colonies from the plate of (5) and inoculating a broth culture to grow vegetative rods; and (7) Repeating steps (1)(a) to (6) between about 10 to about 35 times.

In an example, the two or more single colonies of (6) are three single colonies. Also, steps (1)(a) to (6) are repeated about 15 to about 30 times, or about 17 to about 26 times, and the parameters of (3) may comprise time of spore colonisation, oncolysis, pus formation and burst, tumour volume, systemic toxicity, animal survival, number of spores/rods isolated from the tumours after intravenous administration of spores or any combination thereof.

The process produces bacterial strains that lyse about 20% to about 90%, or about 20% to about 70%, or about 20% to about 40%, or about 20% to about 35%, or about 25% to about 35% of cells within the microenvironment of the tumour.

The process of culturing and harvesting clostridial spores as described herein may be scaled up. Techniques for scaling up are known in the art and contemplated herein.

Kits

As contemplate herein, the present invention provides a kit for the treatment of one or more solid malignant tumours comprising the bacterial strain, the clostridial spores or the pharmaceutical composition as described and defined herein, and further comprising an anti-cancer agent. Instructions for using the kits are also provided.

Other Features of the Invention

The present invention is useful for any subject that has the potential to grow and/or harbour solid tumours. The subject may be a mammal, a human for example, but any animal is contemplated herein and falls within the scope of the invention.

As contemplated herein, examples of solid malignant tumours that may be treated by the present invention are, but not limited to, respiratory system carcinomas, gastrointestinal system carcinomas, genitourinary system carcinomas, testicular carcinomas, breast carcinomas, prostate carcinomas, endocrine system carcinomas, melanomas, choriocarcinoma, and carcinomas of the cervix, lung, head and neck, colon, ovary, brain, bladder, breast, prostate, tumors of bone, fat, and cartilage, Hodgkin's disease, non-Hodgkin's lymphoma, B cell lymphoma, epitheliotropic lymphoma, composite lymphoma, anaplastic large cell lymphoma, gastric and non-gastric mucosa-associated lymphoid tissue lymphoma, lymphoproliferative disease, T cell lymphoma, Burkitt's lymphoma, mantle cell lymphoma, diffuse large cell lymphoma, lymphoplasmacytoid lymphoma, and multiple myeloma.

Compositions, Dosages and Routes of Administration

The derived bacterial strains (and spores therefrom) of the present invention are useful as therapeutic agents in treating solid tumour cancers and are contemplated as a single therapy or as a component in a combination therapy. These bacterial strains find use, for example, in arresting growth of, regressing or destroying one or more solid tumours in a subject, by administering a therapeutically effective amount of spores of the bacterial strains to the subject. Solid tumours can be found for example in the head and neck, back, colon and lungs.

The spores of the derived bacterial strains may be administered by standard routes and one of skill in the art will realize that specific types of cancer can be effectively targeted using specific modes of administration. In general, the derived bacterial strains (spores therefrom) may be administered by the parenteral such as intravenous, intraspinal, subcutaneous or intramuscular. Preferably, the spores are injected into the animal body. For administration of the spores as an injectable solution or suspension, non-toxic parenterally acceptable diluents or carriers can include, Ringer's solution, isotonic saline, phosphate buffered-saline, ethanol and 1,2 propylene glycol.

Methods for preparing parenterally administrable compositions including spores of the present invention are apparent to those skilled in the art, and are described in more detail in, for example, Remington's Pharmaceutical Science, 15th ed., Mack Publishing Company, Easton, Pa., hereby incorporated by reference herein.

Spores of the present invention and other anti-cancer agents such as antibodies may be administered to subjects as compositions/components in a combination therapy. In a therapeutic application, compositions are administered to a subject already possessing a solid tumour cancer, in an amount sufficient to destroy or at least arrest growth of the tumour. The composition should provide a quantity of spores and other anti-cancer agents such as antibodies sufficient to effectively treat the subject.

The anti-cancer agent(s) is any agent that may be used in chemotherapy, radiation, or antibody-based therapies or combinations thereof. The agent may be one or more chemicals, one or more RNA molecules, one or more antibodies or any combination thereof.

For example, the one or more chemicals may be sodium dichloroacetate, paclitaxel, doxil, topotecan, DNA-altering drugs, carboplatin, antimetabolites, gemcitabine, drugs that prevent cell division, vincristine, anti-angiogenic agents, and pazopanib.

An example of the one or more RNA molecules is a small interference RNA (siRNA). The siRNA may be specific for lactate dehydrogenase A (LDHA) or specific for CD147.

An example of the one or more antibodies is an anti-cancer monoclonal antibody which is described below.

The therapeutically effective dose level for any particular patient or subject will depend upon a variety of factors including: the type of solid tumour; size of solid tumour; what additional agents, if any, are used in a combination therapy together with other related factors well known in medicine.

One skilled, in the art would be able by routine experimentation and in view of this disclosure to determine an effective, non-toxic amount of clostridial spores and other agents which would be required to arrest tumour growth of, regress or destroy one or more solid tumours.

Generally, a therapeutically effective amount of clostridial spores of the present invention to treat solid tumours, such as colon and lung, in a human is about $10^6$ colony-forming unit (CFU) to about $10^{14}$ CFU per dose or about $10^8$-$10^{12}$ CFU per dose or about $10^{10}$-$10^{11}$ CFU per dose or about $10^{10.5}$ CFU per dose. In a non-limiting example, administration of the therapeutically effective amount of the clostridial spores is intravenous, intraspinal, subcutaneous or intramuscular. For example, preferred administration is intravenous.

Typically, in therapeutic applications, the treatment would be for the duration of the disease state.

There is also contemplation of a medicament comprising,
(1) a therapeutically effective amount of one or more clostridial spores according to claim 16 and
(2) a therapeutically effective amount of an anti-cancer agent,
for its use in treating one or more solid malignant tumours in a subject, wherein tumour regression is indicative of the treatment, wherein the method comprises administration of the medicament to said subject. There is contemplation of manufacture of the medicament as well.

Further, it will be apparent to one of ordinary skill in the art that the optimal quantity and spacing of individual dosages will be determined by the nature and extent of tumour formation and type of tumour. Also, such optimum conditions can be determined by conventional techniques.

For combination therapies, each component of the combination therapy may be administered at, the same time, or sequentially in any order, or at different times, so as to provide the desired effect. Alternatively, the components may be formulated together in a single dosage unit as a combination product. When administered separately, it may be preferred for the components to be administered by the same route of administration, although it is not necessary for this to be so.

Antibodies

The present invention provides antibodies that are administered to a subject in combination with the clostridial spores of the new derived bacterial strains of the present invention. An effective combinatorial therapy of treating solid tumours whereby tumour regression is indicative of the treatment as contemplated herein could include the clostridial spores of the new derived bacterial strains of the present invention and anti-cancer monoclonal antibodies although any suitable antibody is contemplated herein and includes, but not limited to polyclonal, monoclonal, chimeric, humanised, single chain, Fab fragments, and an Fab expression library. Antibody fragments and analogues are also contemplated.

An anti-cancer antibody as contemplated herein includes an anti-immune stimulation antibody or an anti-T reg monoclonal antibody. An example of an anti-immune stimulation antibody is an anti-CD40 monoclonal antibody. The anti-CD40 monoclonal antibody may be FGK45. An example of an anti-T reg monoclonal antibody is an anti-CD25 monoclonal antibody. The anti-CD25 monoclonal antibody may be PC61. In another embodiment, the agent is targeting anti-epidermal growth factor receptor (EGFR). The agent may be in the form of an anti-EGFR monoclonal antibody, and more specifically, a chimeric (mouse/human) anti-EGFR monoclonal antibody such as Cetuximab for use in treating colorectal, colon, and head and neck cancers, for example. Other anti-EGFR monoclonal antibodies contemplated herein are Panitumumab, Zalutumumab, Nimotuzumab, and Matuzumab. Other agents for targeting EGFR are small molecule EGFR tyrosine kinase inhibitors, such as Gefitinib, Erlotinib and Lapatinib. They may be used to treat, for example, lung cancers (e.g, NSCLC), breast cancers and pancreatic cancers. Natural inhibitors of EFGR are contemplated herein and include potato carboxypeptidase inhibitor (PCI), which contains a small cysteine-rich module, called a T-knot scaffold, that is shared by several different protein families, including the EGF family. Grandinin is another natural EGFR inhibitor. It is an ellagitannin found in *Melaleuca quinquenervia* leaves and in oaks. It has the ability to suppress the phosphorylation of the epidermal growth factor receptor in human colon carcinoma cells.

The anti-cancer monoclonal antibody could be conjugated or naked. Naked antibodies, for example, have an effect such as by complement-mediated cytolysis and antibody-dependent, cell-mediated cytotoxicity. Conjugated antibodies include antibodies that are conjugated to a radioisotope or a drug-activating enzyme. The radioactively conjugated antibody may be used in radioimmunotherapy. Examples of a radioactively conjugated antibody or radioisotope is rhenium-188 or rhenium-186, fluorodeoxyglucose ($^{18}$F) also known as FDG, yttrium 90 ($^{90}$Y)-conjugated anti-CD20 antibody $Y^{90}$-ibritumomab tiuxetan and the iodine 131 ($^{131}$I)-conjugated anti-CD20 antibody $I^{131}$-tositumomab. Antibodies conjugated to a drug-activating enzyme could be used in antibody-directed enzyme prodrug therapy (ADEPT). The anti-cancer monoclonal antibody could be conjugated to a liposome or nanoparticle and include within the liposome or nanoparticle various drugs and therapeutic nucleotides, such as siRNAs.

Anti-cancer monoclonal antibodies can be targeted against malignant cells by several mechanisms. As contemplated herein, such mechanisms include (1) radioimmunotherapy (RIT) which involves the use of radioactively conjugated murine antibodies against cellular antigens (2) Antibody-directed enzyme prodrug therapy (ADEPT) which involves the application of cancer associated monoclonal antibodies which are linked to a drug-activating enzyme whereby subsequent systemic administration of a non-toxic agent results in its conversion to a toxic drug, resulting in a cytotoxic effect which can be targeted at malignant cells and (3) immunoliposomes which are antibody-conjugated liposomes that carry drugs or therapeutic nucleotides, and when conjugated with monoclonal antibodies, may be directed against malignant cells.

Methods for the generation of suitable antibodies will be readily appreciated by those skilled in the art. For example, a monoclonal antibody may be prepared using the hybridoma technology described in Antibodies-A Laboratory Manual, Harlow and Lane, eds., Cold Spring Harbor Laboratory, N.Y. (1988).

In essence, in the preparation of monoclonal antibodies, fragments or analogues thereof, any technique that provides for the production of antibody molecules by continuous cell lines in culture may be used. These include the hybridoma technique originally developed by Kohler et al., Nature, 256:495-497 (1975), as well as the trioma technique, the human B-cell hybridoma technique [Kozbor et at, Immunology Today, 4:72 (1983)], and the EBV-hybridoma technique to produce human monoclonal, antibodies [Cole et al., in Monoclonal Antibodies and Cancer Therapy, pp. 77-96, Alan R. Liss, Inc., (1985)]. Immortal, antibody-producing cell lines can be created by techniques other than fusion, such as direct transformation of B lymphocytes with oncogenic DNA, or transfection with Epstein-Barr virus. See, e.g., M. Schreier et al., "Hybridoma Techniques" (1980); Hammerling et al., "Monoclonal Antibodies and T-cell Hybridomas" (1981); Kennett et al., "Monoclonal Antibodies" (1980).

In summary, a means of producing a hybridoma from which the monoclonal antibody is produced, a myeloma or other self-perpetuating cell line is fused with lymphocytes obtained from the spleen of a mammal hyperimmunised with a recognition factor-binding portion thereof, or recognition factor, or an origin-specific DNA-binding portion thereof. Hybridomas producing a monoclonal antibody useful in practicing this invention are identified by their ability to immunoreact with the present recognition factor and their ability to inhibit specified transcriptional activity in target cells.

A monoclonal antibody useful in practicing the present invention can be produced by initiating a monoclonal hybridoma culture comprising a nutrient medium containing a hybridoma that secretes antibody molecules of the appropriate antigen specificity. The culture is maintained under conditions and for a time period sufficient for the hybridoma to secrete the antibody molecules into the medium. The antibody-containing medium is then collected. The antibody molecules can then be further isolated by techniques known in the art.

Similarly, there are various procedures known in the art which may be used for the production of polyclonal antibodies, or fragments or analogues thereof. For the production of polyclonal antibody, various host animals can be immunized by injection with the antigen, or a fragment or analogue thereof, including but not limited to rabbits, mice, rats, sheep, goats, etc.

Screening for the desired antibody can also be accomplished by a variety of techniques known in the art. Assays for immunospecific binding of antibodies may include, but are not limited to, radioimmunoassays, ELISAs (enzyme-linked immunosorbent assay), sandwich immunoassays, immunoradiometric assays, gel diffusion precipitation reactions, immunodiffusion assays, in situ immunoassays, Western blots, precipitation reactions, agglutination assays, complement fixation assays, immunofluorescence assays, protein A assays, and immunoelectrophoresis assays, and the like (see, for example, Ausubel et al., eds, 1994, Current Protocols in Molecular Biology, Vol. 1, John Wiley & Sons, Inc., New York). A variety of methods is known in the art for detecting binding in an immunoassay and is within the scope of the present invention.

Antibodies or fragments thereof used to perform the invention has binding affinity or avidity greater than about $10^5$ $M^{-1}$, more preferably greater than about $10^6$ $M^{-1}$, more preferably still greater than about $10^7 M^{-1}$ and most preferably greater than about $10^8 M^{-1}$.

If producing antibody to be used in a combination therapy with the clostridial spores of the new derived bacterial strains of the present invention, one may manufacture the antibody(s) using batch fermentation with serum free medium. After fermentation the antibody may be purified via a multistep procedure incorporating chromatography and viral inactivation/removal steps. For instance, the antibody may be first separated by Protein A affinity chromatography and then treated with solvent/detergent to inactivate any lipid enveloped viruses. Further purification, typically by anion and cation exchange chromatography may be used to remove residual proteins, solvents/detergents and nucleic acids. The purified antibody may be further purified and formulated into 0.9% saline using gel filtration columns. The formulated bulk preparation may then be sterilised and viral filtered and dispensed.

Any antibody design and deimmunization technology that allows for efficacy of treatment and reduction of toxicity of solid tumour cancers is contemplated herein. The conjugation of radioisotopes, small-molecule cytotoxic drugs, and protein toxins to the targeting antibodies and the enhancement of effector function of antibody-dependent cellular cytotoxicity to enhance the efficacy of anticancer antibodies are also contemplated herein. Toxicity has been a major obstacle in the development of therapeutic antibodies for cancer and anti-cancer therapies in general. For antibodies, cross-reactivity with normal tissues can cause significant side effects, including dyspnea from pulmonary toxic effects, occasional central and peripheral nervous system complications, decreased liver function, renal damage, and, on occasion, unexpected toxic effects such as the heart muscle damage associated with the use of trastuzumab for example. In addition, radioimmunotherapy with isotopic-conjugated antibodies also can cause bone marrow suppression. The combinatorial therapeutic approach of using clostridial spores of the new derived bacterial strains with anti-cancer agents, such as antibodies, may reduce the dosage of antibodies required to have a therapeutic effect thus lessening the toxic effects.

Conjugation procedures that complex chemical, drugs, toxins etc to the antibody are contemplated herein. Conjugates to antibodies include a radioisotope and a drug-activating enzyme as contemplated above but also include fungal-derived potent toxins, gemtuzumab ozogamicin, and maytansinoid (DM-1).

Additional Treatments

Radiation therapy is contemplated herein as part of the combinatorial therapeutic approach of regressing solid tumours including use of clostridial spores of the bacterial strains of the present invention. Generally, ionizing radiation would be used as a component of combinatorial cancer treatment to control malignant cells. There are two different ways to deliver radiation to the tissues to be treated:

- a machine called a linear accelerator that delivers radiation from outside the body
- pellets, or seeds, of material that give off radiation beams from inside the body Example of tissues to be treated might include the breast area, lymph nodes, or another part of the body but any solid tumour that may be affected by radiation is contemplated. It is necessary to include a margin of normal tissue around the tumor to allow for uncertainties in daily set-up and internal tumor motion. These uncertainties can be caused by internal movement (for example, respiration and bladder filling) and movement of external skin marks relative to the tumor position. Radiation therapy along with inoculation of clostridial spores of the present invention can be combined with surgery, chemotherapy, hormone therapy, Immunotherapy or some mixture of the four. Most common cancer types can be treated with radiation therapy in some way. The precise treatment intent (curative, adjuvant, neoadjuvant, therapeutic, or palliative) will depend on the tumor type, location, and stage, as well as the general health of the patient. Total body irradiation (TBI) is a radiation therapy technique used to prepare the body to receive a bone marrow transplant. Brachytherapy, in which a radiation source is placed inside or next to the area requiring treatment, is another form of radiation therapy that minimizes exposure to healthy tissue during procedures to treat cancers of the breast, prostate and other organs.

Hormonal therapy is also contemplated herein as a possible aspect of combinatorial therapy for treating solid malignant tumours. Hormonal therapy involves the manipulation of the endocrine system through exogenous administration of specific hormones, particularly steroid hormones, or drugs which inhibit the production or activity of such hormones (hormone antagonists). Because steroid hormones are powerful drivers of gene expression in certain cancer cells, changing the levels or activity of certain hormones can cause certain cancers to cease growing, or even undergo cell death. Surgical removal of endocrine organs, such as orchiectomy and oophorectomy can also be employed as a form of hormonal therapy.

Hormonal therapy is used for several types of cancers derived from hormonally responsive tissues, including, but not limited to, the breast, prostate, endometrium, and adrenal cortex. Hormonal therapy may also be used in the treatment of paraneoplastic syndromes or to ameliorate certain cancer- and chemotherapy-associated symptoms, such as anorexia. Perhaps the most familiar example of hormonal therapy in oncology is the use of the selective estrogen-response modulator tamoxifen for the treatment of breast cancer, although another class of hormonal agents, aromatase inhibitors, now have an expanding role in that disease.

The present invention will now be described with reference to specific examples, which should not be construed as in any way limiting the scope of the invention.

EXAMPLES

The below Examples show the advantages, of the new derived clostridial strains as oncolytic agents compared to other clostridial strains such as excellent specificity, safety and efficacy profiles. It is clear from the Examples that the other clostridial strains including *C. novyi* and *C. sordellii* have the potential to cause oncolysis but nevertheless are highly toxic as their oncolytic effects are too fast, causing significant side/toxic effects, including death to animals bearing the tumours. This limits their use as a clinical modality.

Example 1: Identification, Isolation and Colonisation of the New Derived Clostridial Strains The inventors examined *C. novyi*-NT and *C. sordellii* as well as two saccharolytic species *C. acetobutylicum* and *C. beijerinckii* and compared them with additional proteolytic *Clostridium* spp available (six clinical variants of *C. sodellii*, two *C. bifermentas*, and ATCC No. 25757 (i.e. an avirulent, proteolytic strain of *C. ghonii* which has not been previously reported has an effective anti-cancer agent for solid tumours) in advanced melanoma, colon and lung cancer (0.45 cm$^3$) models, such as xenograft and syngeneic mouse models of advanced non-small cell lung carcinoma (NSCLC).

Figure 1:
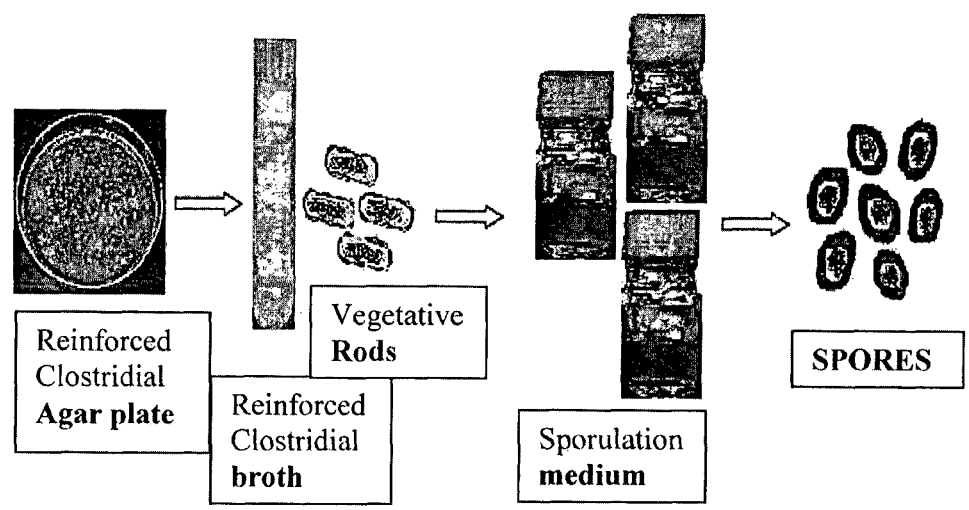
FIG. 1. Schematic representation of spore production. The schematic representation shows that a new aliquot of a clostridial spore suspension is plated on Reinforced Clostridial agar plate in anaerobic conditions for 24 hours. Then up to five colonies are scooped, inoculated in 10 ml HI broth and cultured anaerobically. Twenty four hours later, the culture is then transferred to 50 ml or 100 ml modified sporulation medium and cultured in anaerobic conditions. If it is a tight lid bottle, the culture can be incubated in normal incubator without anaerobic condition. Spores are ready for harvesting in 7 days, but could be harvested as late as 14 days. When harvesting, the bottle is briefly shaken, then left to stay still for a couple of minutes before the top part of the culture is pipetted into a spin bucket bottle, and centrifuged at 5000 g for washing the spores. Purified spores are titrated to determine the titer in colony form unit (CFU). This work will take 2-4 days. The process can be scaled up.

Firstly, the inventors prepared injectable clostridial spores to administer to the models (see FIG. 1—Schematic representation of spore production). The method of effective culturing and harvesting of clostridial spores was discovered by the inventors and comprise the following steps:

Use of a modified sporulation medium comprising, for example;
  Heart Infusion Medium and Reinforced Clostridial Medium are from OXOID.
  Sporulation Medium for 1 Liter pH 7.4 contains:
  Na2HPO4 (Sigma) 5 g
  L cysteine (Sigma) 0.5 g
  Maltose Monohydrate (Chem-Supply) 10 g
  Proteose Peptone (OXOID) 30 g
  Cooked Meat Medium (OXOID) 10%
Use 50-100 mL aliquot, best suits spore production;
Inoculate bacterial rods into sporulation medium contained in a test tube and incubate at 35° C. to grow a culture;
Sporulation will be ready for harvesting in 10 days.
Briefly shake the test tube so that heavy dry meat in the medium will sink to the bottom. Let the culture rest for a couple of minutes, then use a pipet to remove the top part of the culture in the tube and then place into a spin bucket bottle,
Use 5000 g speed to spin the bottle.

Secondly, the clostridial spores were injected into the models and various parameters were assessed such as time of spore colonisation and oncolysis, pus formation and burst, tumour volume (i.e. growth, shrinking or disappearing), systemic toxicity, animal survival as well as the number of spores/rods isolated from the tumours after intravenous administration of spores.

The results showed that while two saccharolytic species and the proteolytic *C. sporogenes* did not exhibit significant colonisation and oncolysis, proteolytic *C. novyi*-NT and *C. sordellii* were indeed highly efficient. 50% of animals bearing advanced tumours started to have oncolysis at 12 hours after i.v. injection and finished by 24 hours. The tumour went through necrosis with skin colour changes from purple to black, accompanied by pus/liquid formation and tumour skin rupture while the host animal looked lethargic and sick, an obvious sign of toxicity due to rapid tumour lysis.

Figure 2:
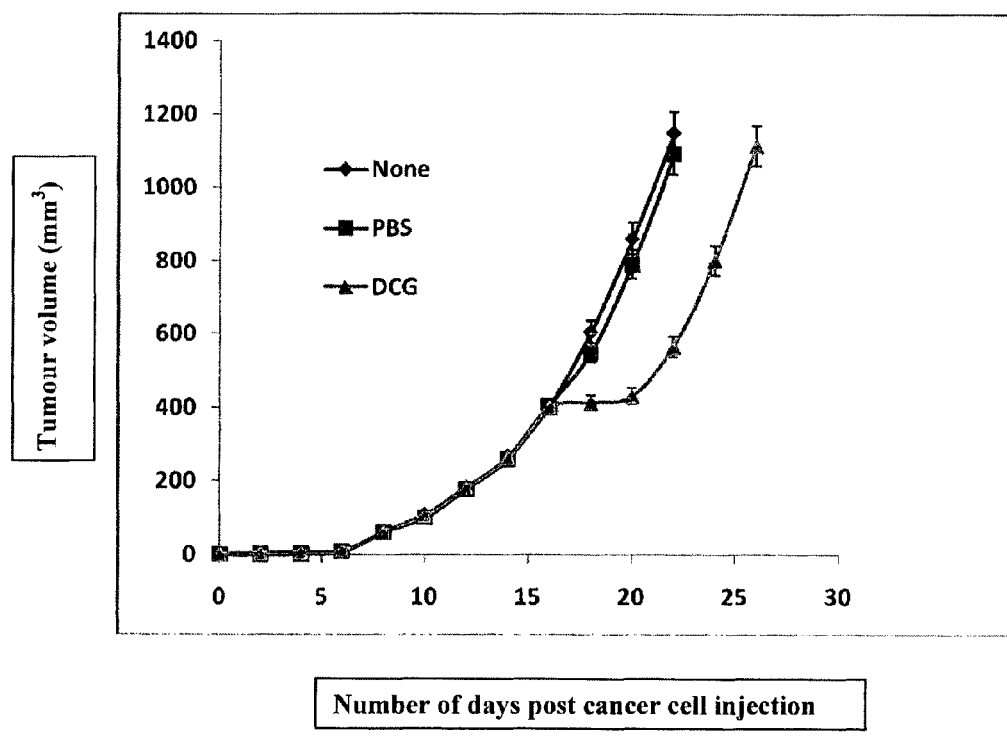
FIG. 2. Oncolytic capacity of the derived bacterial strains. Mice were randomised into 3 groups. On day 15, group 1 was left with no injection as a control (denoted as 'None' in the figure key legend), Group 2 administered with phosphate buffer saline (denoted as 'PBS' in the figure key legend), and group 3 was administered with the spores of a derived bacterial strain (denoted as 'DOG' in the figure key legend). Tumour volume was recorded every other day. The DCG group showed a delayed tumour growth in tumour volumes.

In contrast, ATCC No. 25757 was slower in establishing colonisation and oncolysis, but was more efficient in oncolysis in both xenograft and syngeneic mouse model of NSCLC. Spore colonisation was evident at 48 hours and oncolysis at 72 hours which lasted more than 10 days after spore administration. However, the oncolytic ability of the wild type *C. ghonii* is variable, thus on average, it is not significantly different to the avirulent strain of *C. ghonii* (ATCC No. 25757) but it is clear that the avirulent strain had oncolysis and tumour growth delay (see FIG. 2). Importantly and surprisingly, this strain was not associated with toxicity in contrast to the other clostridial strains.

Figure 3:
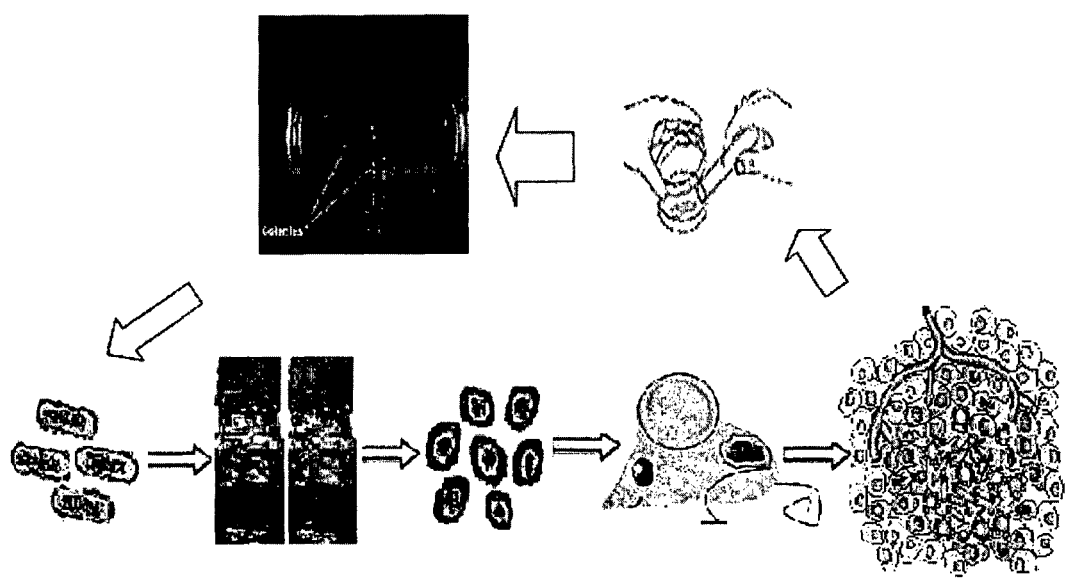
FIG. 3. Schematic representation of spore delivery and repeated adaptation of Clostridial spores. Mice (n=3) bearing tumors of different sizes (detectable to 0.45 $cm^3$) are i.v. injected with $10^8$ CFU of spores. Tumor growth and volume in the mice are evaluated every other day using both ultrasound as well as digital callipers. In addition, the length of time before the tumour skin colour changes, tumour necrosis/liquid/pus formation, and liquid/pus/tumour skin burst, the time and number of spores in the tumours, tumour growth/shrinkage/disappearance as well as any toxic signs and animal behaviour changes are assessed. Only those tumours that show liquid/pus/tumor skin burst or necrosis/liquid/pus formation at 80% are excised and homogenized. Lysates of these tumours are used for plating on agar plates for further and repetitive clostridial culture isolation. The adaptation progress is repeated depending on the type of the tumours.

Like the wild-type strain, the spores from the avirulent strain that were injected into the mice models had a variable oncolytic effect. To improve the consistency of *C. ghonii*'s oncolytic effect, the inventors discovered a method for improvement of consistency by repeatedly adapting, selecting and re-isolating the strain for 26 cycles (see Example 2 below and FIG. 3 for a schematic diagram of the method). Eventually, the inventors isolated a new derivative of the avirulent *C. ghonii* strain that has superior capacity to penetrate, colonise and thrive in melanoma, colon and lung cancers over other known clostridial strains considered useful in treating cancer.

Example 2: Adaptation to Achieve New Derived Clostridial Strains

The avirulent *C. ghonii* strain was repeatedly adapted in three tumour models: (1) an advanced NSCLC (A549) (2) Colon cancer model (HCT116) and (3) Head and neck (HN5) cancer. Tumours used for adaptation in each group (n=6) completed oncolysis. Clostridial rods were collected from within the tumour inoculated by spores of the avirulent *C. ghonii* strain, ATCC No. 25757, by harvesting the solid tumour and then homogenising the tumour tissues, which were then streaked out on a Reinforced Clostridial Medium/agar plate. Three single colonies from the plates were then pooled in a 40 ml of Reinforced Clostridial Medium broth culture and incubated under anaerobic condition at 37° C. overnight. For sporulation, the 40 ml bacterial culture was added to 1 Liter of sporulation medium (0.5% $Na_2HPO_4$, 3% thiotone E peptone, 0.05% L cysteine, 1% maltose, 5% dried cooked meat particle, pH 7.4) and incubated under anaerobic condition at 37° C. for 2 weeks. At this time point, clostridia have formed endospores and were ready for purification. To purify the spores, 200 ml of spore suspension was first centrifuged at 12,000 rpm for 15 min at 4° C. The resulted pellet was then resuspended and washed twice with 200 ml of cold PBS followed by centrifugation. After wash, the spore pellet was resuspended with cold PBS and sonicated for 5 min on ice to release endospores and deplete vegetative cells. Following sonification, the spores were washed another 6-10 times using cold PBS until the spore suspension is cleared of cell debris. The purity of the spore suspension was finally confirmed by phase contrast microscopy to have <1% vegetative cell material and designated as strain MW-DCG_LCv12.

Resuspended spores of MW-DCG_LCv12 at appropriate concentrations, for example at $5 \times 10^7 - 1 \times 10^8$ CFU; were injected into tail veins of the models for subsequent reinoculation of new tumours of NSCLC (i.e. lung), colon and Head and Neck cancer while reisolating the new variant strains.

Figure 4:
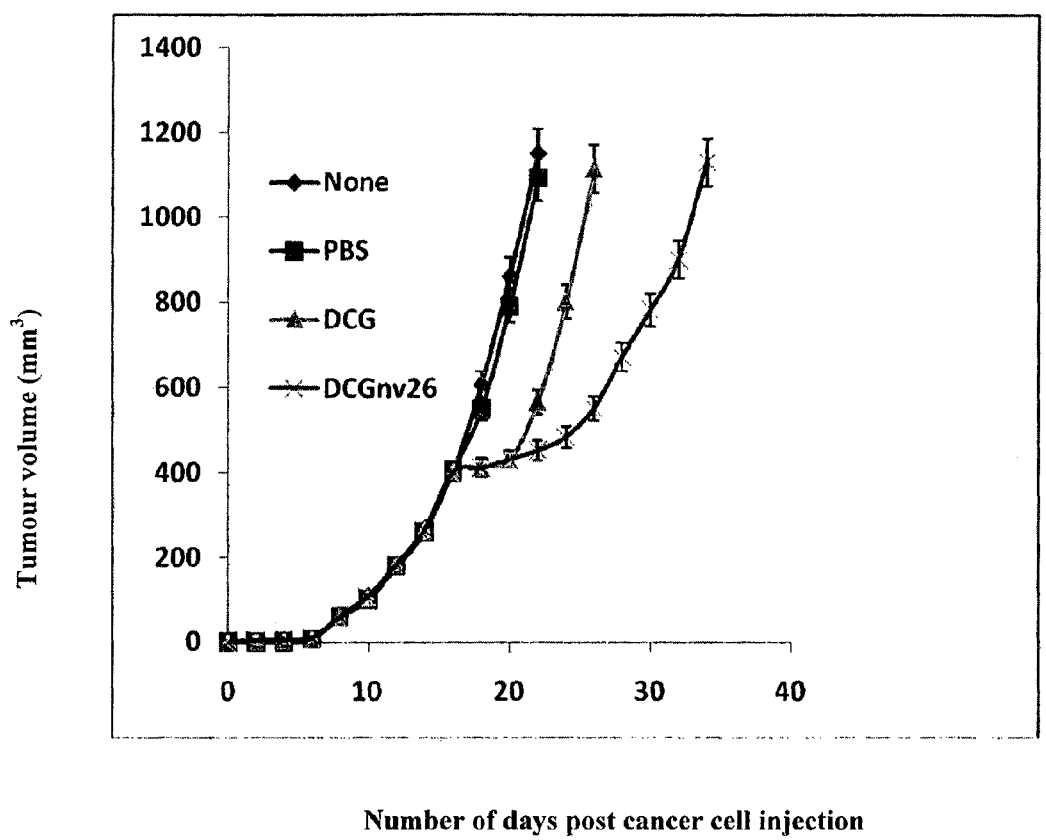
FIG. 4. Oncolytic capacity of MW-DCG_LCv26 (referred in the figure as DCGnv26) in Lung cancer (NSCLC) (A549) model. Mice were randomised into 4 groups. On day 15, group 1 was left with no injection as a control, Group 2 administered with PBS, 3 with DCG and 4 with MW-DCG_LCv26 spores. Tumour volume was recorded every other day.
Figure 5:
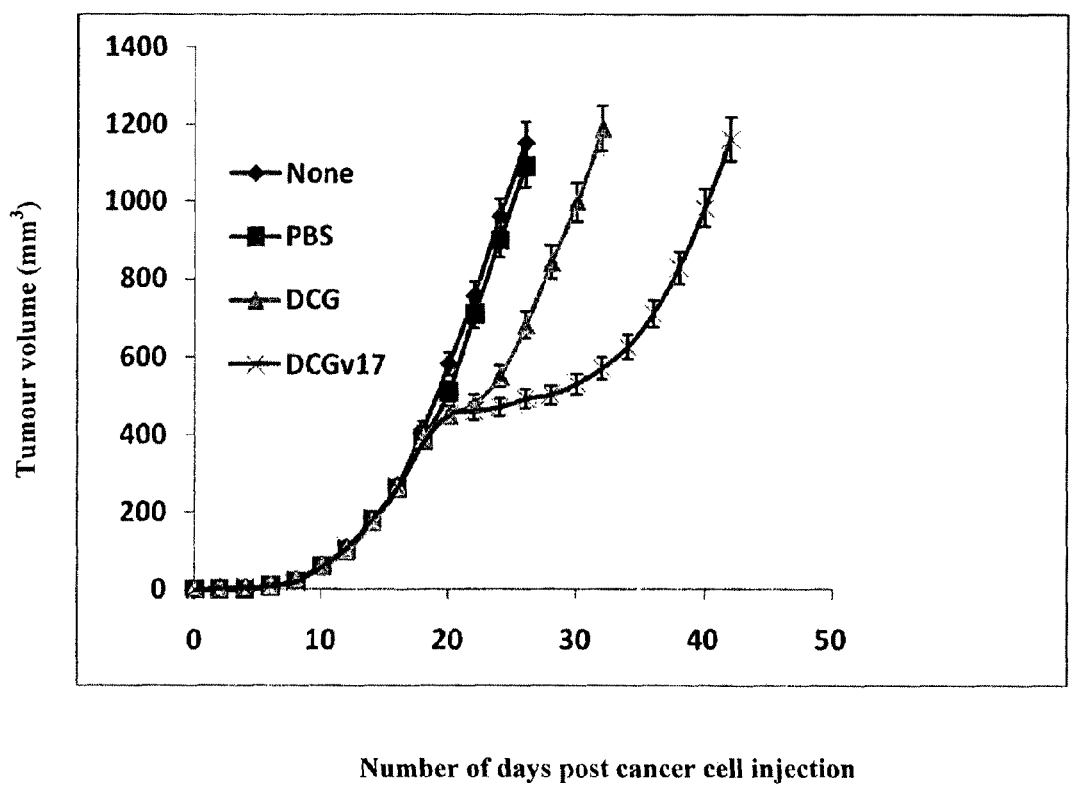
FIG. 5. Oncolytic capacity of MW-DCG_CCv17 (referred in the figure as DCGv17) in colon cancer model. Mice were randomised into 4 groups. On day 15, group 1 was left with no injection as a control, Group 2 administered with PBS, 3 with DCG and 4 with MW-DCG_CCv17 spores. Tumour volume was recorded every other day.
Figure 6:
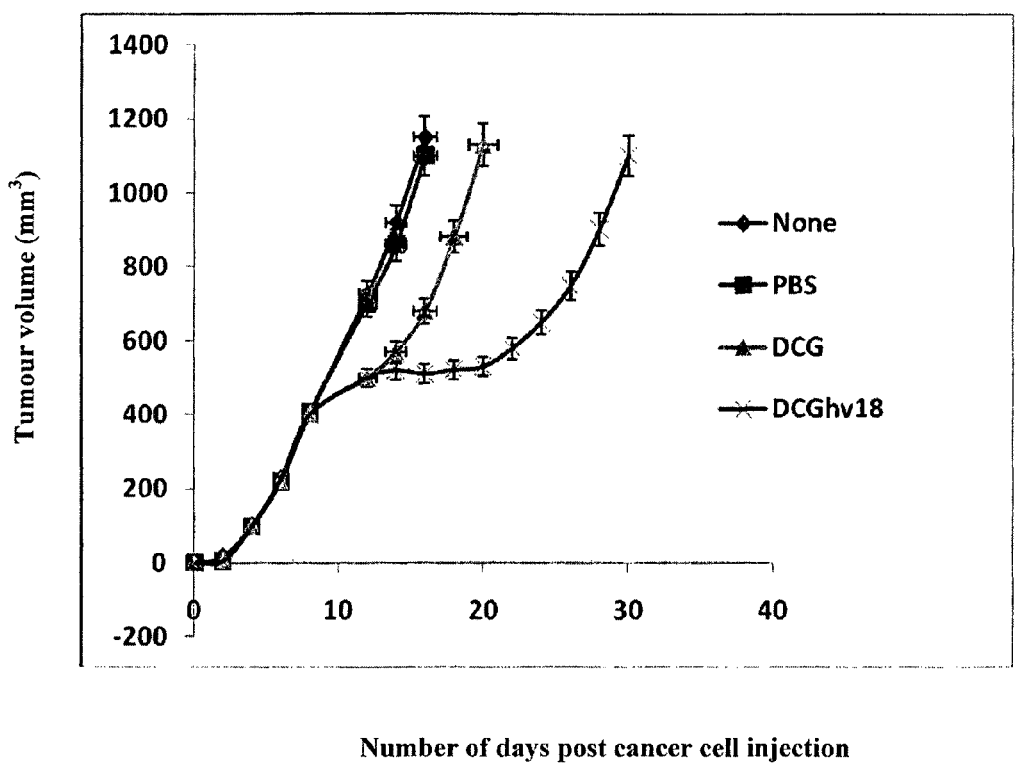
FIG. 6. Oncolytic capacity of MW-DCG_HNCv18 (referred in the figure as DCGhv18) in head and neck cancer model. Mice were randomised into 4 groups. On day 15, group 1 was left with no injection as a control, Group 2 administered with PBS, 3 with DCG and 4 with MW-DCG_HNCv18 spores. Tumour volume was recorded every other day.

After 17-26 such repeated cycles, the inventors isolated several new derived bacterial strains that have superior properties over the non-adapted, avirulent *C. ghonii* such as assured capacity of penetrating, colonising, thriving and causing significant oncolysis in NSCLC, colon cancer and Head and Neck cancer, without any visiable toxic effects. Oncolysis were accompanied with tumour significant growth delay as per FIGS. 4 to 6 but without toxicity/sign of toxicity that is associated with previous studies using clostridia such as *C. novyi*-NT and *C. sordellii*. This is very significant, as the protocol of repeated isolation, and adaptation have never been used in such a way.

These new derived bacterial strains caused near complete tumour destruction via oncolysis (necrosis) in 30% of mice bearing advanced melanoma and lung cancer. These mice were monitored for a further three months and showed no evidence of tumour reappearance. In the remaining mice there were also various degrees of oncolysis and retardation of tumour growth. The new derived bacterial strains that would be most effective in a combinatorial therapy for treating solid tumours would be specific to the type of solid tumours (e.g. colon cancer), result in greater than 20% necrosis of cancer cells located inside the tumour and have low to no toxicity as measured and compared to a reference clostridial strain. Strains that meet these criteria which are specific for and effective against solid tumours of NSCLC, colon, and Head and Neck cancers are described below.

NSCLC

A total of 26 isolates (strains) were adapted specifically for NSCLC (lung cancer) and include MW-DCG_LCv1, MW-DCG_LCv2, MW-DCG_LCv3, MW-DCG_LCv4, MW-DCG_LCv5, MW-DCG_LCv6, MW-DCG_LCv7, MW-DCG_LCv8, MW-DCG_LCv9, MW-DCG_LCv10, MW-DCG_LCv11, MW-DCG_LCv12, MW-DCG_LCv13, MW-DCG_LCv14, MW-DCG_LCv15, MW-DCG_LCv16, MW-DCG_LCv17, MW-DCG_LCv18, MW-DCG_LCv19, MW-DCG_LCv20, MW-DCG_LCv21, MW-DCG_LCv22, MW-DCG_LCv23, MW-DCG_LCv24, MW-DCG_LCv25 and MW-DCG_LCv26. Out of the 26 isolates, data for three preferred isolates are provided in the table below. Toxicity level is defined and scored using a comprehensive score sheet including the following four levels: Appearance; Clinical Signs; Unprovoked behaviour; and Behavioral responses to external stimuli. MW-DCG_LCv26 is a strain that resulted in a high percentage of necrosis of a solid tumour of NSCLC in the mouse model with no toxicity other than tumour lysis syndrome (which is a manifestation of the mouse model).

| Isolate/Strain No | Number of CFU isolated | Percentage of necrosis | Day/tumour volume | Days of mouse survival* | Tumour lysis syndrome | Toxicity Level |
|---|---|---|---|---|---|---|
| MW-DCG_LCv1 | 2-3 | 26% | 25/1 $cm^3$ | 25 | Yes (0) | No |
| MW-DCG_LCv12 | 10-12 | 40% | 28/1 $cm^3$ | 28 | Yes (+) | No |
| MW-DCG_LCv26 | 150-160 | 65% | 34/1 $cm^3$ | 34 | Yes (++) | No (other than TLS) |

Colon Cancer

A total of 17 isolates (strains) were adapted specifically for colon cancer and include MW-DCG_LCv1, MW-DCG_LCv2, MW-DCG_LCv3, MW-DCG_LCv4, MW-DCG_LCv5, MW-DCG_LCv6, MW-DCG_LCv7, MW-DCG_LCv8, MW-DCG_LCv9, MW-DCG_LCv10, MW-DCG_LCv11, MW-DCG_LCv12, MW-DCG_CCv13, MW-DCG_CCv14, MW-DCG_CCv15, MW-DCG_CCv16 and MW-DCG_CCv17. Out of the 17 isolates, data for four preferred isolates are provided in the table below. Toxicity level is defined and scored using a comprehensive score sheet including the following four levels: Appearance; Clinical Signs; Unprovoked behaviour; and Behavioral responses to external stimuli. MW-DCG_CCv17 is a strain that resulted in a high percentage of necrosis of a solid tumour of colon cancer in the mouse model with no toxicity other than tumour lysis syndrome (which is a manifestation of the mouse model).

| Isolate/Strain No | Number of CFU isolated | Percentage of necrosis | Day/tumour volume | Days of mouse survival* | Tumour lysis syndrome | Toxicity Level |
|---|---|---|---|---|---|---|
| MW-DCG_LCv1 | 2-3 | 26% | 25/1 $cm^3$ | 25 | Yes (0) | No |
| MW-DCG_LCv12 | 10-12 | 40% | 28/1 $cm^3$ | 28 | Yes (+) | No |

-continued

| Isolate/<br>Strain No | Number<br>of<br>CFU<br>isolated | Percentage<br>of<br>necrosis | Day/<br>tumour<br>volume | Days of<br>mouse<br>survival* | Tumour<br>lysis syndrome | Toxicity<br>Level |
|---|---|---|---|---|---|---|
| MW-DCG_CCv13 | 15-30 | 40% | 30/1 cm$^3$ | 30 | Yes (+) | No |
| MW-DCG_CCv17 | 150-160 | 70% | 42/1 cm$^3$ | 42 | Yes (++) | No (other than TLS) |

Head and Neck Cancer

A total of 18 isolates (strains) were adapted specifically for Head and Neck cancer and include MW-DCG_LCv1, MW-DCG_LCv2, MW-DCG_LCv3, MW-DCG_LCv4, MW-DCG_LCv5, MW-DCG_LCv6, MW-DCG_LCv7, MW-DCG_LCv8, MW-DCG_LCv9, MW-DCG_LCv10, MW-DCG_LCv11, MW-DCG_LCv12, DCG_HNCv13, MW-DCG_HNCv14, MW-DCG_HNCv15, MW-DCG_HNCv16, MW-DCG_HNCv17 and MW-DCG_HNCv18. Out of the 18 isolates, data for three preferred isolates are provided in the table below. Toxicity level is defined and scored using a comprehensive score sheet including the following four levels: Appearance; Clinical Signs; Unprovoked behaviour; and Behavioral responses to external stimuli. MW-DCG_HNCv18 is a strain that resulted in a high percentage of necrosis of a solid tumour of Head and Neck cancer in the mouse model with no toxicity other than tumour lysis syndrome (which is a manifestation of the mouse model).

| Isolate/<br>Strain No | Number of<br>CFU isolated | Percentage<br>of<br>necrosis | Day/<br>tumour<br>volume | Days of<br>mouse<br>survival* | Tumour<br>lysis<br>syndrome | Toxicity<br>Level |
|---|---|---|---|---|---|---|
| MW-DCG_LCv1 | 2-3 | 26% | 25/1 cm$^3$ | 25 | Yes (0) | No |
| MW-DCG_LCv12 | 10-12 | 40% | 28/1 cm$^3$ | 28 | Yes (+) | No |
| MW-DCG_HNCv13 | 10-15 | 30% | 20/1 cm$^3$ | 20 | Yes (+) | No |
| MW-DCG_HNCv18 | 150-160 | 70% | 32/1 cm$^3$ | 32 | Yes (++) | No (other than TLS) |

In summary, the strain MW-DCG_HNCv18 which is specific for and effective against solid tumours of Head and Neck cancer, the strain MW-DCG_CCv17 which is specific for and effective against solid tumours of colon cancer, the strain MW-DCG_LCv26 which is specific for and effective against solid tumours of NSCLC have superior properties over the non-adapted, avirulent *C. ghonii* such as assured capacity of penetrating, colonising, th dose of Cetuximab treatment. Mice treated with combination therapy extended their survival to over 80 days, an almost 4 folds extension of life span.

All of the compositions and methods disclosed and claimed herein can be made and executed without undue experimentation in light of the present disclosure. While the compositions, methods, uses and processes of this invention have been described in terms of preferred embodiments, it will be apparent to those of skill in the art that variations may be applied to the compositions and methods, and in the steps or in the sequence of steps of the methods and processes described and defined herein without departing from the concept, spirit and scope of the invention. More specifically, it will be apparent that certain agents which are both chemically and physiologically related may be substituted for the agents described herein while the same or similar results would be achieved. All such similar substitutions and modifications apparent to those skilled in the art are deemed to be within the spirit, scope and concept of the invention as defined by the appended claims.

The invention claimed is:

1. A composition comprising a bacterial strain and a pharmaceutically-acceptable carrier, wherein the bacterial strain is MW-DCG_HNCv18, wherein the bacterial strain is capable of arresting growth of, regressing or destroying a solid tumor of a head and neck cancer, and wherein the bacterial strain comprises a polyclonal mixture of bacterial cells.

2. A composition comprising a bacterial strain and a pharmaceutically-acceptable carrier, wherein the bacterial strain is MW-DCG_CCv17, wherein the bacterial strain is capable of arresting growth of, regressing or destroying a solid tumor of a colon cancer, and wherein the bacterial strain comprises a polyclonal mixture of bacterial cells.

3. A composition comprising a bacterial strain and a pharmaceutically-acceptable carrier, wherein the bacterial strain is MW-DCG_LCv26, wherein the bacterial strain is capable of arresting growth of, regressing or destroying a solid tumor of a non-small cell lung cancer (NSCLC), and wherein the bacterial strain comprises a polyclonal mixture of bacterial cells.

4. The composition of any one of claims 1-3, wherein the bacterial strain is produced by a method comprising the steps of:
   (1) injecting a plurality of injectable clostridial spores into an animal that supports growth of a solid tumor, wherein the plurality of injectable clostridial spores generate a plurality of vegetative rods upon contacting the tumor;
   (2) assessing one or more parameter(s) to determine rate and degree of oncolysis and toxicity of the plurality of vegetative rods of (1);
   (3) collecting the plurality of vegetative rods from the tumor of (2);
   (4) streaking out the plurality of vegetative rods of (3) onto a plate;
   (5) selecting two or more single colonies from the plate of (4)
   (6) culturing the two or more single colonies in a broth culture to produce a second or subsequent plurality of vegetative rods
   (7) culturing the second or subsequent plurality of vegetative rods in a sporulation medium under conditions sufficient to produce a second or subsequent plurality of injectable clostridial spores;
   (8) purifying the second or subsequent plurality of injectable clostridial spores, and
   (9) repeating steps (1) to (8) between about 17 to about 26 times.

5. The composition of claim 4, wherein the animal that supports growth of a solid tumor is a mouse.

6. The composition of claim 4 or 5, wherein the solid tumor comprises a xenograft of human tumor cells.

7. The composition of any one of claims 4-6, wherein the steps (1) to (8) are repeated from about 15 to about 30 times.

8. The composition of any one of claims 4-6, wherein the steps (1) to (8) are repeated from about 10 to about 35 times.

9. The composition of any one of claims 4-8, wherein the one or more parameter(s) of step (2) comprise time of spore colonization, oncolysis, pus formation and burst, tumor volume, systemic toxicity, animal survival, number of spores and/or rods isolated from the tumors after intravenous administration of spores or any combination thereof.

10. The composition of any one of claims 4-9, wherein the bacterial strain oncolyses cells contained within the microenvironment of the tumor.

11. The composition of any one of claims 4-10, wherein the bacterial strain oncolyses about 20% to about 90% of cells within the microenvironment of the tumor.

12. The composition of any one of claims 4-10, wherein the bacterial strain oncolyses about 20% to about 70% of cells within the microenvironment of the tumor.

13. The composition of any one of claims 4-10, wherein the bacterial strain oncolyses 20% to about 40% of cells within the microenvironment of the tumor.

14. The composition of any one of claims 4-10, wherein the bacterial strain oncolyses about 20% to about 35% of cells within the microenvironment of the tumor.

15. The composition of any one of claims 4-10, wherein the bacterial strain oncolyses about 25% to about 35% of cells within the microenvironment of the tumor.

16. The composition of any one of claims 4-15, wherein the bacterial strain causes less toxicity than a reference clostridial strain.

17. The composition of any one of claims 4-16, further comprising an excipient.

18. A method of arresting the growth of, regressing or destroying one or more solid malignant tumors of a head and neck cancer in a subject, comprising administering to the subject a therapeutically effective amount of the composition of claim 1.

19. A method of arresting the growth of, regressing or destroying one or more solid malignant tumors of a colon cancer in a subject, comprising administering to the subject a therapeutically effective amount of the composition of claim 2.

20. A method of arresting the growth of, regressing or destroying one or more solid malignant tumors of a NSCLC in a subject, comprising administering to the subject a therapeutically effective amount of the composition of claim 3.

21. The method of any one of claims 18 to 20, wherein the method further comprises administering a therapeutically effective amount of an anti-cancer agent.

* * * * *